(12) United States Patent
Cahoon

(10) Patent No.: US 6,855,870 B2
(45) Date of Patent: Feb. 15, 2005

(54) PLANT CINNAMYL-ALCOHOL DEHYDROGENASE HOMOLOGS

(75) Inventor: Rebecca C. Cahoon, Webster Groves, MO (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 181 days.

(21) Appl. No.: 10/357,886

(22) Filed: Feb. 4, 2003

(65) Prior Publication Data

US 2003/0159170 A1 Aug. 21, 2003

Related U.S. Application Data

(62) Division of application No. 09/501,115, filed on Feb. 9, 2000, now Pat. No. 6,552,249.
(60) Provisional application No. 60/119,585, filed on Feb. 10, 1999.

(51) Int. Cl.[7] .......................... A01H 1/00; C07H 21/04; C07K 14/415; C12N 5/14; C12N 9/00
(52) U.S. Cl. .......................... 800/295; 435/6; 435/69.1; 435/468; 435/419; 435/252.3; 435/320.1; 435/183; 530/370; 536/23.6; 800/278
(58) Field of Search .......................... 435/6, 69.1, 468, 435/419, 252.3, 320.1, 183; 530/370; 536/23.6; 800/278, 295

(56) References Cited

PUBLICATIONS

Helentjaris et al., N_GeneSeq Database, Accession No. AAX25205, WO9910498, Mar. 4, 1999.*
Bork, P. Genome Research. vol. 10, p. 398–400, 2000.*
Vance, C.P. et al., (1980), Annu. Rev. Phytopathol., 18:259–288.
Boudet, A. et al., 1996, Mol. Breeding 2:25–39.
Campbell, M. et al., (1996), Plant Phys., 110:3–13.
NCBI General Identifier No. 4097522.
NCBI General Identifier No. 3603401.
Plant Mol. Biol., 41(2):279–291 (1999) Brill et al.
NCBI General Identifier No. 1724110.
NCBI General Identifier No. 6648160.
NCBI General Identifier No. 3913194.
NCBI General Identifier No. 1168727.
Plant Cell Phys., 34:659–665 (1993) Hibino et al.
NCBI General Identifier No. 399168.
Plant Phys. Biochem., 33:105–109 (1995) Doorsselaere et al.
NCBI General Identifier No. 3913181.
NCBI General Identifier No. 6323980.
Science 274 (5287):546(1996) Goffeau et al.
Nature 387 (6632 Suppl):90–93 (1997) Bowman et al.
Claire Halpin et al., Brown–Midrib Maize (BM1)—A Mutation Affecting The Cinnamyl Alcohol Dehydrogenase Gene, The Plant Journal (1998) 14(5A), 545–553.
Marie Andree et al., Effect of Down–Regulation of Cinnamyl Alcohol Dehydrogenase on Cell Wall Composition and on Degradability of Tobacco Stems, J. Sci.I Food AGIC. 1998, 76, 505–514.

* cited by examiner

Primary Examiner—Phuong T. Bui

(57) ABSTRACT

This invention relates to an isolated nucleic acid fragment encoding a lignin biosynthetic enzyme. The invention also relates to the construction of a chimeric gene encoding all or a portion of the lignin biosynthetic enzyme, in sense or antisense orientation, wherein expression of the chimeric gene results in production of altered levels of the lignin biosynthetic enzyme in a transformed host cell.

11 Claims, No Drawings

SEQUENCE LISTING

<160> NUMBER OF SEQ ID NOS: 48

<210> SEQ ID NO 1
<211> LENGTH: 1339
<212> TYPE: DNA
<213> ORGANISM: Oryza sativa

<400> SEQUENCE: 1

```
gcacgaggtt ctaaccgccg gcgagaaacc tgcagagggc gagggcgagt gcggcggagc      60
aggggatgga ggagcatggc aaggcggctg tcggctgggc ggccagggac gactccggcg     120
tcctctcccc gtacaacttc tccaggaggg ctcagaagga cgatgacgtc accatcaagg     180
tgctctactg cggcatctgc cacactgacc tgcacatcgt caagaatgat tggggcaacg     240
ccatgtaccc cgtcgtcccc ggccacgaga tcgtcggcgt cgtcaccggc gtcggcgccg     300
gcgtgaccaa gttcaaggcc ggcgacacgg tgggcgtggg ctacttcgtc gcgtcgtgcc     360
gcggctgcga gtgctgcggg aatgggtacg agaactactg cgccaagatg gtaaccacct     420
gcaacggcgt cgaccacgac cacggcggcg gcgcggccac ccagggcggc ttctccgacg     480
ccatcgtcgt caacgagcac tacgtgctcc gcgtgccggc ggggctgccg ctggacagcg     540
cggcgccgct gctgtgcgcc ggcgtgacgg tgtacagccc gatggtgatc cacggcctga     600
acgcgccggg gaagcacgtc ggcgtcgtcg gcctcggcgg gctcggccac gtcgccgtca     660
agttcgccaa ggcgttcggg atgcgcgtca ccgtcatcag cacgtcgccg gggaagcggc     720
aggaggcact ggagcacctc ggcgccgacg agttcctcgt cagccgcgac gcgggccaga     780
tggcggcggc ggcggccacc atggacggga tcctcaacac ggtgtcggcc tggcacccga     840
tcgcgccgct gttctcgctg atgaagccga tggcgcagat ggtgttcgtc ggcgggccga     900
ccaggccgct ggagctgccg gcgtacgcca tcgtgcccgg agggaagggc atcaccggca     960
actgcgtcgg cggcatcagg gactgccagg ccatgctcga cttcgccggc gagcacggca    1020
tcactgccga ggtggaggtc atcaagatgg actacgtcaa cacggcgatg gagcggctgg    1080
agaagaacga tgtccgctac cgcttcgtca tcgacgttgc cggcagcagc ctcgccggct    1140
ccggcgacgc caagatataa agctcgccgg cttgcttgct tgcttgtgtc gacggcgccg    1200
gcgccgccta gcttgcttgt tgtgtgtcag tggcctgaa tgtttggtga tgtgcaaact    1260
actacgaaat ggagtaagaa ataagtggag catatgtctc catcacttgg ttattaatta    1320
aaaaaaaaaa aaaaaaaa                                                  1339
```

<210> SEQ ID NO 2
<211> LENGTH: 364
<212> TYPE: PRT
<213> ORGANISM: Oryza sativa

<400> SEQUENCE: 2

Met Glu Glu His Gly Lys Ala Ala Val Gly Trp Ala Ala Arg Asp Asp

```
         1               5              10              15
Ser Gly Val Leu Ser Pro Tyr Asn Phe Ser Arg Arg Ala Gln Lys Asp
                20                  25                  30

Asp Asp Val Thr Ile Lys Val Leu Tyr Cys Gly Ile Cys His Thr Asp
                35                  40                  45

Leu His Ile Val Lys Asn Asp Trp Gly Asn Ala Met Tyr Pro Val Val
 50                  55                  60

Pro Gly His Glu Ile Val Gly Val Val Thr Gly Val Gly Ala Gly Val
 65                  70                  75                  80

Thr Lys Phe Lys Ala Gly Asp Thr Val Gly Val Gly Tyr Phe Val Ala
                85                  90                  95

Ser Cys Arg Gly Cys Glu Cys Cys Gly Asn Gly Tyr Glu Asn Tyr Cys
                100                 105                 110

Ala Lys Met Val Thr Thr Cys Asn Gly Val Asp His Asp His Gly Gly
                115                 120                 125

Gly Ala Ala Thr Gln Gly Gly Phe Ser Asp Ala Ile Val Val Asn Glu
                130                 135                 140

His Tyr Val Leu Arg Val Pro Ala Gly Leu Pro Leu Asp Ser Ala Ala
145                 150                 155                 160

Pro Leu Leu Cys Ala Gly Val Thr Val Tyr Ser Pro Met Val Ile His
                165                 170                 175

Gly Leu Asn Ala Pro Gly Lys His Val Gly Val Val Gly Leu Gly Gly
                180                 185                 190

Leu Gly His Val Ala Val Lys Phe Ala Lys Ala Phe Gly Met Arg Val
                195                 200                 205

Thr Val Ile Ser Thr Ser Pro Gly Lys Arg Gln Glu Ala Leu Glu His
                210                 215                 220

Leu Gly Ala Asp Glu Phe Leu Val Ser Arg Asp Ala Gly Gln Met Ala
225                 230                 235                 240

Ala Ala Ala Ala Thr Met Asp Gly Ile Leu Asn Thr Val Ser Ala Trp
                245                 250                 255

His Pro Ile Ala Pro Leu Phe Ser Leu Met Lys Pro Met Ala Gln Met
                260                 265                 270

Val Phe Val Gly Gly Pro Thr Arg Pro Leu Glu Leu Pro Ala Tyr Ala
                275                 280                 285

Ile Val Pro Gly Gly Lys Gly Ile Thr Gly Asn Cys Val Gly Gly Ile
                290                 295                 300

Arg Asp Cys Gln Ala Met Leu Asp Phe Ala Gly Glu His Gly Ile Thr
305                 310                 315                 320

Ala Glu Val Glu Val Ile Lys Met Asp Tyr Val Asn Thr Ala Met Glu
                325                 330                 335

Arg Leu Glu Lys Asn Asp Val Arg Tyr Arg Phe Val Ile Asp Val Ala
                340                 345                 350

Gly Ser Ser Leu Ala Gly Ser Gly Asp Ala Lys Ile
                355                 360
```

<210> SEQ ID NO 3
<211> LENGTH: 1463
<212> TYPE: DNA
<213> ORGANISM: Glycine max

<400> SEQUENCE: 3

```
attacccaag ytcgaaatka acctcactaa agggaacaaa agctggagct ccaccgcggt      60
ggcggccgct ctagaactag tggatccccc gggctgcagg aattcggcac gagcagcaaa     120
```

```
gggaaaagca acagagtgt ctaatcgaag atagaagaag agatggctaa atctccagaa      180
actgaacttc ccgtcgaagc tttcggttgg gctgcttcag acacttctgg cacccttgca      240 cctttcatt tctccagaag agaaaatggc gttgatgacg tcactctcaa gattctcttc       300 tgcgggttt gccactcgga tctccacact ctcaaaaacg actggggttt caccacttac       360
cctgtcgttc ctgggcatga aattgttggt gttgtgacaa agttggcaa caatgtgaaa       420 aacttcaaag tgggtgataa agttggagtt ggtgtgatag tggagtcttg caaggaatgt      480
gaaagttgcc aacaagatct ggagagttac tgtccccgcc ctgtttttac ctataactct      540
ccttattatg atgggacacg aaccaaacgt ggttattcta acatcatggt tgtgcaccag      600
cgttatgtgc tccgatttcc tgagaacttg cctcttgatg ctggtgctcc tctgctgtgt      660
gctgggataa ctgtgtatag cccgatgaaa tattatggga tgacagagcc aggcaaacat      720 ttggagtgg cagggcttgg tgggttaggt catgttgcaa tcaaacttgc taaggcgttt       780
gggctgaagt tactgtcatc cagtagctct cctaacaagc aagctgaggc cattgaccga      840 ctcgggctg attctttcct tgtttcatca gaccctgcaa aaatgaaggt ggctttggga       900
accatggact atatcataga cacaatttct gctgttcatt ccctgattcc actgcttggt      960
ctgctgaagc tgaatgggaa gctagttact gtagggttgc ctaacaagcc ccttgagctt     1020
cctatctttc cattagttgc aggacggaaa cttataggg ggagcaactt tggagggatc      1080
aaagaaactc aggaaatgct tgatttctgc gcaaagcaca acataactgc agatattgag     1140
ctgattaaga tggatcagat caacacagcc atggaaaggc ttagcaaagc tgatgtgaaa     1200
tatcgctttg tgattgatgt ggcgaactct ttcgcaagtt tgtagaagcc accatgattc     1260
tccaactctt tgcatgtgtg gcctttagat gtctcagtat tttgaaagta gattggtggt     1320
ataagtagtc tataagatgt tgaactttaa agatgagaac atctgctaat taataatact     1380
ttgggttttg aatttatatt atgttccttt aaaaaaaaa aaaaaaaaa aaactcgagg      1440 ggggggcccgg tacccaattc gcc                                             1463
```

<210> SEQ ID NO 4
<211> LENGTH: 360
<212> TYPE: PRT
<213> ORGANISM: Glycine max

<400> SEQUENCE: 4

```
Met Ala Lys Ser Pro Glu Thr Glu Leu Pro Val Glu Ala Phe Gly Trp
  1               5                  10                  15

Ala Ala Ser Asp Thr Ser Gly Thr Leu Ala Pro Phe His Phe Ser Arg
             20                  25                  30

Arg Glu Asn Gly Val Asp Asp Val Thr Leu Lys Ile Leu Phe Cys Gly
         35                  40                  45

Val Cys His Ser Asp Leu His Thr Leu Lys Asn Asp Trp Gly Phe Thr
     50                  55                  60

Thr Tyr Pro Val Val Pro Gly His Glu Ile Val Gly Val Thr Lys
 65                  70                  75                  80

Val Gly Asn Asn Val Lys Asn Phe Lys Val Gly Asp Lys Val Gly Val
                 85                  90                  95

Gly Val Ile Val Glu Ser Cys Lys Glu Cys Glu Ser Cys Gln Gln Asp
            100                 105                 110

Leu Glu Ser Tyr Cys Pro Arg Pro Val Phe Thr Tyr Asn Ser Pro Tyr
        115                 120                 125
```

```
Tyr Asp Gly Thr Arg Thr Lys Arg Gly Tyr Ser Asn Ile Met Val Val
130                 135                 140

His Gln Arg Tyr Val Leu Arg Phe Pro Glu Asn Leu Pro Leu Asp Ala
145                 150                 155                 160

Gly Ala Pro Leu Leu Cys Ala Gly Ile Thr Val Tyr Ser Pro Met Lys
                165                 170                 175

Tyr Tyr Gly Met Thr Glu Pro Gly Lys His Leu Gly Val Ala Gly Leu
                180                 185                 190

Gly Gly Leu Gly His Val Ala Ile Lys Leu Ala Lys Ala Phe Gly Leu
            195                 200                 205

Lys Leu Leu Ser Ser Ser Ser Pro Asn Lys Gln Ala Glu Ala Ile
210                 215                 220

Asp Arg Leu Gly Ala Asp Ser Phe Leu Val Ser Ser Asp Pro Ala Lys
225                 230                 235                 240

Met Lys Val Ala Leu Gly Thr Met Asp Tyr Ile Ile Asp Thr Ile Ser
                245                 250                 255

Ala Val His Ser Leu Ile Pro Leu Leu Gly Leu Leu Lys Leu Asn Gly
                260                 265                 270

Lys Leu Val Thr Val Gly Leu Pro Asn Lys Pro Leu Glu Leu Pro Ile
                275                 280                 285

Phe Pro Leu Val Ala Gly Arg Lys Leu Ile Gly Gly Ser Asn Phe Gly
290                 295                 300

Gly Ile Lys Glu Thr Gln Glu Met Leu Asp Phe Cys Ala Lys His Asn
305                 310                 315                 320

Ile Thr Ala Asp Ile Glu Leu Ile Lys Met Asp Gln Ile Asn Thr Ala
                325                 330                 335

Met Glu Arg Leu Ser Lys Ala Asp Val Lys Tyr Arg Phe Val Ile Asp
                340                 345                 350

Val Ala Asn Ser Phe Ala Ser Leu
                355                 360

<210> SEQ ID NO 5
<211> LENGTH: 1414
<212> TYPE: DNA
<213> ORGANISM: Triticum aestivum

<400> SEQUENCE: 5
gcacgagtcg tggttagtga ttacgaccag caagtcacaa gtgagggcgg agaggttga     60 ggttgaggaa gagcagagga atccattcca ggagtgttta atggcgggag caaggaagc    120 gcacgggtgg gcagccaggg atgtctctgg tcacctctcc ccttaccact tctcacggag    180
ggttcagaga gacgacgacg tcaccatcaa ggtgctcttc tgcgggcttt gccacactga    240
cctccacgtc atcaagaacg agtttggcaa cgccaagtac cccgtcgttc ccgggcacga    300
gatcgtcggc gtcgtcaccg acgtcggctc cggcgtcaca agcttcaagc ccggcgacac    360
ggtgggcgtg ggctacttcg tcgactcctg ccgcagctgc gacagctgca gcaagggta    420 cgagagctac tgcccgcagc tcgtggagac gtccaacggc gtgagcctgg acgacgatga    480
cggcggcgcc accaccaagg gcggcttctc cgacgccctc gtcgtccacc agcgctacgt    540
ggtgcgggtc ccggccagcc tgccgccgc cggggccgcg ccgctgctgt gcgccggcgt    600
caccgtgttc agcccatgg tgcagtacgg cctgaacgcg ccggggaagc acctgggcgt    660
cgtcggcctc ggcggcctcg gccacctggc cgtccgcttc ggcaaggcgt tcggatgaa    720 ggtcaccgtc atcagcacgt cgctgggcaa gcgggacgag gccctcggcc gcctcggtgc    780
```

-continued

```
cgacgcgttc ctggtcagcc gcgaccccga gcagatgagg gcggcggcgg gcaccttgga    840
cggcgtcatc gacacggtgt cggccgacca ccctgtcgtg ccgctgctgg acctgctcaa    900
gccgatgggc cagatggtcg tcgtcggcct gcccaccaag ccgctccagg tgcctgcctt    960
cagcctcgtc gccggcggga agcgcgtggc cgggagtgcc ggcggcggcg tcggggagtg   1020
ccaggccatg ctcgactttg ccggcgagca cgggatcacc gcggatgtgg aggtcgtcgg   1080
gatggactac gtcaataccg ccatccagcg cctagagagg aacgatgtca ggtaccgctt   1140
cgttgtcgac gtcgcgagca gcaagattgg aggctaggca tcaccattcc tagtgttctg   1200
tcgatcgacg tgtgatttgc ttcttcctcg agcgtgtctt attgttctgg ttggagcacg   1260
tacgcggcca tcacacgcag gcgtggacaa taaacaaggt agagtttcgg gttgtgtcgt   1320
taaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaa                               1414
```

<210> SEQ ID NO 6
<211> LENGTH: 358
<212> TYPE: PRT
<213> ORGANISM: Triticum aestivum

<400> SEQUENCE: 6

```
Met Ala Gly Gly Lys Glu Ala His Gly Trp Ala Ala Arg Asp Val Ser
  1               5                  10                  15

Gly His Leu Ser Pro Tyr His Phe Ser Arg Arg Val Gln Arg Asp Asp
                 20                  25                  30

Asp Val Thr Ile Lys Val Leu Phe Cys Gly Leu Cys His Thr Asp Leu
             35                  40                  45

His Val Ile Lys Asn Glu Phe Gly Asn Ala Lys Tyr Pro Val Val Pro
         50                  55                  60

Gly His Glu Ile Val Gly Val Thr Asp Val Gly Ser Gly Val Thr
     65                  70                  75                  80

Ser Phe Lys Pro Gly Asp Thr Val Gly Val Gly Tyr Phe Val Asp Ser
                 85                  90                  95

Cys Arg Ser Cys Asp Ser Cys Ser Lys Gly Tyr Glu Ser Tyr Cys Pro
            100                 105                 110

Gln Leu Val Glu Thr Ser Asn Gly Val Ser Leu Asp Asp Asp Asp Gly
        115                 120                 125

Gly Ala Thr Thr Lys Gly Gly Phe Ser Asp Ala Leu Val Val His Gln
    130                 135                 140

Arg Tyr Val Val Arg Val Pro Ala Ser Leu Pro Pro Ala Gly Ala Ala
145                 150                 155                 160

Pro Leu Leu Cys Ala Gly Val Thr Val Phe Ser Pro Met Val Gln Tyr
                165                 170                 175

Gly Leu Asn Ala Pro Gly Lys His Leu Gly Val Val Gly Leu Gly Gly
            180                 185                 190

Leu Gly His Leu Ala Val Arg Phe Gly Lys Ala Phe Gly Met Lys Val
        195                 200                 205

Thr Val Ile Ser Thr Ser Leu Gly Lys Arg Asp Glu Ala Leu Gly Arg
    210                 215                 220

Leu Gly Ala Asp Ala Phe Leu Val Ser Arg Asp Pro Glu Gln Met Arg
225                 230                 235                 240

Ala Ala Ala Gly Thr Leu Asp Gly Val Ile Asp Thr Val Ser Ala Asp
                245                 250                 255

His Pro Val Val Pro Leu Leu Asp Leu Leu Lys Pro Met Gly Gln Met
```

-continued

```
                 260                 265                 270
        Val Val Val Gly Leu Pro Thr Lys Pro Leu Gln Val Pro Ala Phe Ser
                    275                 280                 285

Leu Val Ala Gly Gly Lys Arg Val Ala Gly Ser Ala Gly Gly Val
            290                 295                 300

Gly Glu Cys Gln Ala Met Leu Asp Phe Ala Gly Glu His Gly Ile Thr
        305                 310                 315                 320

Ala Asp Val Glu Val Val Gly Met Asp Tyr Val Asn Thr Ala Ile Gln
                        325                 330                 335

Arg Leu Glu Arg Asn Asp Val Arg Tyr Arg Phe Val Val Asp Val Ala
                    340                 345                 350

Ser Ser Lys Ile Gly Gly
                    355
```

<210> SEQ ID NO 7
<211> LENGTH: 1409
<212> TYPE: DNA
<213> ORGANISM: Zea mays
<220> FEATURE:
<221> NAME/KEY: unsure
<222> LOCATION: (270)
<220> FEATURE:
<221> NAME/KEY: unsure
<222> LOCATION: (389)
<220> FEATURE:
<221> NAME/KEY: unsure
<222> LOCATION: (1306)
<220> FEATURE:
<221> NAME/KEY: unsure
<222> LOCATION: (1334)
<220> FEATURE:
<221> NAME/KEY: unsure
<222> LOCATION: (1339)
<220> FEATURE:
<221> NAME/KEY: unsure
<222> LOCATION: (1354)
<220> FEATURE:
<221> NAME/KEY: unsure
<222> LOCATION: (1391)

<400> SEQUENCE: 7

```
cagaagtaga atcattcgat tccccaaagc gaaatccgca gcctcgcctc tctcgccatt      60
ttccaggcgc gcgctcggcg cggccgccgc cagcgataca gatccttgca cggacacaag    120
ggctccgcgc tcccaccgga tcggatcccg tcccgatggc tcccactccc actcacacgg    180
cggcggcgt ggcgctcgcc gcgcacgact cgtccggcca cctcgcgccg ctcaccatca     240
cccgcaggag caccggggac gacgatgtan cgataaagat cctgtactgt gggatgtgtc    300
actctgacct tcacagcatc aagaacgagt ggcacaacgc cacgtacccc atggtccctg    360
gtcacgagat cgccggagtg gtgacggang tgggcaagaa cgtgaccagc ttcaaggccg    420
gggaccgcgt cggcgtgggc tgcatggtga actcgtgcca gtcgtgcggc agctgcgacg    480
aggacttcga gaacagctgc cgggccgtca tcttcaccta caactccgtc gaccgcgacg    540
gcaccgtcac ctacgcggc tactccagca gcgtggtggt gcacgagcgc ttcgtggtcc     600
ggttccccga cgcgatgccg ctggatcggg gggcgccgct gctgtgcgcg gcatcacag     660
tgtacagccc catgaagtac acggcctga acgtgccggg gaagcacgtc ggcgtgatgg     720
ggctgggagg cctgggccac gtcgccgtca gttcgccaa ggcgttcggg gccaaggtca    780
cggtcatcag cacgtcgcct gggaagaaga aggaggcgct cgaccggctt ggcgccgacg    840
ccttcgtcgt cagcaaggac gccgaagaaa tgaaggcggc tgcgagcacc atggacggca    900
```

-continued

```
tcatcaacac ggtgtcggcg aacctcacct tggccccgta catgggcctg ctcaagccca      960
acggcaagat gatcatggtc ggcctgccca ccaagcctct cgagatcccg cccttttgatc    1020 tcatcattgg gaacaagacc ctggccggga gctgcatcgg cggcatgagg gacacgcagg    1080
agatgatcaa cgtggcggcc aagcacggcg tgacggcgga catagaactg gtggccgcgg    1140
actacgtgaa cacggccatg gagcgcctgg ccaaggctga cgtcaggtac cgcttcgtca    1200
tcgacatcgg caacacctca agaatcagag tgtcagacta aaacccggcg acactctact    1260
gctgctgctg ttgtccttcg ctttatacat gaacgctcct ttttcntgtc atgataatat    1320
taactaagca actnactant ccgaggatct ccanctgtat gaattggtct tatgtgttcc    1380
taaacagata natcacattt taaaaaaaa                                      1409
```

<210> SEQ ID NO 8
<211> LENGTH: 361
<212> TYPE: PRT
<213> ORGANISM: Zea mays
<220> FEATURE:
<221> NAME/KEY: UNSURE
<222> LOCATION: (39)
<220> FEATURE:
<221> NAME/KEY: UNSURE
<222> LOCATION: (78)

<400> SEQUENCE: 8

```
Met Ala Pro Thr Pro Thr His Thr Ala Ala Val Ala Leu Ala Ala
 1               5                  10                  15

His Asp Ser Ser Gly His Leu Ala Pro Leu Thr Ile Thr Arg Arg Ser
                20                  25                  30

Thr Gly Asp Asp Val Xaa Ile Lys Ile Leu Tyr Cys Gly Met Cys
         35                  40                  45

His Ser Asp Leu His Ser Ile Lys Asn Glu Trp His Asn Ala Thr Tyr
     50                  55                  60

Pro Met Val Pro Gly His Glu Ile Ala Gly Val Val Thr Xaa Val Gly
 65                  70                  75                  80

Lys Asn Val Thr Ser Phe Lys Ala Gly Asp Arg Val Gly Val Gly Cys
                 85                  90                  95

Met Val Asn Ser Cys Gln Ser Cys Gly Ser Cys Asp Glu Asp Phe Glu
                100                 105                 110

Asn Ser Cys Arg Ala Val Ile Phe Thr Tyr Asn Ser Val Asp Arg Asp
            115                 120                 125

Gly Thr Val Thr Tyr Gly Gly Tyr Ser Ser Val Val Val His Glu
        130                 135                 140

Arg Phe Val Val Arg Phe Pro Asp Ala Met Pro Leu Asp Arg Gly Ala
145                 150                 155                 160

Pro Leu Leu Cys Ala Gly Ile Thr Val Tyr Ser Pro Met Lys Tyr His
                165                 170                 175

Gly Leu Asn Val Pro Gly Lys His Val Gly Val Met Gly Leu Gly Gly
                180                 185                 190

Leu Gly His Val Ala Val Lys Phe Ala Lys Ala Phe Gly Ala Lys Val
            195                 200                 205

Thr Val Ile Ser Thr Ser Pro Gly Lys Lys Gln Glu Ala Leu Asp Arg
        210                 215                 220

Leu Gly Ala Asp Ala Phe Val Val Ser Lys Asp Ala Glu Glu Met Lys
225                 230                 235                 240

Ala Ala Ala Ser Thr Met Asp Gly Ile Ile Asn Thr Val Ser Ala Asn
                245                 250                 255
```

Leu Thr Leu Ala Pro Tyr Met Gly Leu Leu Lys Pro Asn Gly Lys Met
        260                 265                 270

Ile Met Val Gly Leu Pro Thr Lys Pro Leu Glu Ile Pro Pro Phe Asp
        275                 280                 285

Leu Ile Ile Gly Asn Lys Thr Leu Ala Gly Ser Cys Ile Gly Gly Met
        290                 295                 300

Arg Asp Thr Gln Glu Met Ile Asn Val Ala Ala Lys His Gly Val Thr
305                 310                 315                 320

Ala Asp Ile Glu Leu Val Ala Ala Asp Tyr Val Asn Thr Ala Met Glu
                325                 330                 335

Arg Leu Ala Lys Ala Asp Val Arg Tyr Arg Phe Val Ile Asp Ile Gly
        340                 345                 350

Asn Thr Ser Arg Ile Arg Val Ser Asp
        355                 360

<210> SEQ ID NO 9
<211> LENGTH: 1480
<212> TYPE: DNA
<213> ORGANISM: Oryza sativa

<400> SEQUENCE: 9
gcacgagctt acatgtaagc tcgtgccgaa ttcggcacga gcttacactc tcatcctctc      60
ctctcccact ccacacccag gcacccagct cgagcgcgac tcggcaaatc catggctccc     120
acggcggcgt cggcggcggc gggggaggag cagcaggcgg tggggctggc ggcgcgcgac     180
tcctccggcc acctctcccc tttcgccatc tcccgaggag gcactggaga tgacgatgtg     240
gcgataaaga ttctgttctg tggaatctgc cactctgacc tgcactgcat caagaatgag     300
tggaagcact ccatctaccc acttgttcct gggcacgaga tcgccggtgt ggtgacggag     360
gtggggaaga acgtcaccag gttcaaggcc ggcgacaggg tcggcgtggg gtgcatggtg     420
aactcgtgcc ggtcatgcga gagctgtaac aatggcttcg agaaccactg cccggagggc     480
gtcttcacct acaactccgt cgacaaggac ggcaccgtca cctacggcgg ttactcgagc     540
atggtggtgg tgcacgagcg cttcgtggtc atgttcccgg aggcgatgcc gctcgacgtc     600
ggcgccccgc tgctgtgcgc cggcatcacc gtgtacaccc ccatgaagta ccacggcctg     660
aacgcgccgg ggaagcacgt cggcgtgctc ggcctgggcg ggctcggcca cgtcgcggtg     720
aagttcgcca gggcgttcgg gttgaaggtg acggtgatca gctcgtcgcc ggggaagaag     780
cgggaggcgc tggagcggct cggcgccgac gcgttcgtcg tgagcagcag cgccgaggag     840
atggaggccg cgaggtccac catggacggc gtcatcaaca cggtctccgc caacaccccc     900
atggcgccgt acctggcgtt gctgaagccc aacgggaaga tgatcctcgt cggcctcccg     960
gagaatcccc tggaggtccc tcccttctct ctcgtccacg ggaacaggac tctggcaggg    1020
agcaacatcg gcggcatggc ggacacgcag gagatgatcg agctggcggc gaagcacggc    1080
gtgacggcgg acatcgaggt gatcggcgcc gacgacgtga acacggccat ggagcgcctc    1140
gccaaggcgg atgtcaggta tcgcttcgtc atcgacgtcg ggaacaccct ccacgccgcc    1200
gccgccgagt gatggcatcg cctgcaaact attcgtgtgg tctgtaatct gtatgaaatt    1260
gttcatggta cgtacacgat atatagattg tggcgtgtca tggcgtatag gaatgaaccc    1320
gatcgaggaa gctattgttg gtagtctgat gctagtcagc tcagtgtttg actgtttgca    1380
tttacggatt gaaattgagc tttgtgtggc ctaagtttta ttttctaaag atttcaagtg    1440
aatttcgttt tattcgaatg aaaaaaaaaa aaaaaaaaa                           1480

<210> SEQ ID NO 10
<211> LENGTH: 366
<212> TYPE: PRT
<213> ORGANISM: Oryza sativa

<400> SEQUENCE: 10

```
Met Ala Pro Thr Ala Ala Ser Ala Ala Gly Glu Glu Gln Gln Ala
 1               5                  10                  15

Val Gly Leu Ala Ala Arg Asp Ser Ser Gly His Leu Ser Pro Phe Ala
                20                  25                  30

Ile Ser Arg Arg Ser Thr Gly Asp Asp Val Ala Ile Lys Ile Leu
            35                  40                  45

Phe Cys Gly Ile Cys His Ser Asp Leu His Cys Ile Lys Asn Glu Trp
        50                  55                  60

Lys His Ser Ile Tyr Pro Leu Val Pro Gly His Glu Ile Ala Gly Val
 65                 70                  75                  80

Val Thr Glu Val Gly Lys Asn Val Thr Arg Phe Lys Ala Gly Asp Arg
                85                  90                  95

Val Gly Val Gly Cys Met Val Asn Ser Cys Arg Ser Cys Glu Ser Cys
            100                 105                 110

Asn Asn Gly Phe Glu Asn His Cys Pro Glu Gly Val Phe Thr Tyr Asn
        115                 120                 125

Ser Val Asp Lys Asp Gly Thr Val Thr Tyr Gly Gly Tyr Ser Ser Met
    130                 135                 140

Val Val His Glu Arg Phe Val Val Met Phe Pro Glu Ala Met Pro
145                 150                 155                 160

Leu Asp Val Gly Ala Pro Leu Leu Cys Ala Gly Ile Thr Val Tyr Thr
                165                 170                 175

Pro Met Lys Tyr His Gly Leu Asn Ala Pro Gly Lys His Val Gly Val
            180                 185                 190

Leu Gly Leu Gly Gly Leu Gly His Val Ala Val Lys Phe Ala Arg Ala
        195                 200                 205

Phe Gly Leu Lys Val Thr Val Ile Ser Ser Pro Gly Lys Lys Arg
    210                 215                 220

Glu Ala Leu Glu Arg Leu Gly Ala Asp Ala Phe Val Val Ser Ser Ser
225                 230                 235                 240

Ala Glu Glu Met Glu Ala Ala Arg Ser Thr Met Asp Gly Val Ile Asn
                245                 250                 255

Thr Val Ser Ala Asn Thr Pro Met Ala Pro Tyr Leu Ala Leu Leu Lys
            260                 265                 270

Pro Asn Gly Lys Met Ile Leu Val Gly Leu Pro Glu Asn Pro Leu Glu
        275                 280                 285

Val Pro Pro Phe Ser Leu Val His Gly Asn Arg Thr Leu Ala Gly Ser
    290                 295                 300

Asn Ile Gly Gly Met Ala Asp Thr Gln Glu Met Ile Glu Leu Ala Ala
305                 310                 315                 320

Lys His Gly Val Thr Ala Asp Ile Glu Val Gly Ala Asp Asp Val
                325                 330                 335

Asn Thr Ala Met Glu Arg Leu Ala Lys Ala Asp Val Arg Tyr Arg Phe
            340                 345                 350

Val Ile Asp Val Gly Asn Thr Leu His Ala Ala Ala Glu
        355                 360                 365
```

<210> SEQ ID NO 11
<211> LENGTH: 1389
<212> TYPE: DNA
<213> ORGANISM: Glycine max

<400> SEQUENCE: 11

```
gcacgagcag agatggagca tccaaagaag gtttttggtt gggctgctcg ggactcatct      60
gggcttctct ccccattcaa cttctccaga agagaaacgg gggagaaaga tttggtattc     120
aaagtgcaat actgtggaat atgccactca gatctacata tgttaaagaa cgagtggggc     180
aacacaacct atcctctggt tcctgggcac gagattgctg gtgtggtaac agaagttgga     240
agcaaggtgc aaaagttcaa agttggagac cgggtaggtg tggggtgcat gattggatcc     300
tgtcgttcat gtgaaagctg tgatgaaaat cttgagaatt actgcccccaa atgattctc     360
acatacggtg tcaagtattt tgatggcacc ataacacatg gaggctactc tgacttgatg     420
gttgcggatg aacactttgt ggttagaatt ccggataacc taccacttga tgctgctgct     480
cctctcctct gtgctgggat cactgtgtat agcccttttga gatactatgg acttgacaag     540
cctggtctga tcttggtgt ggttggtctt ggtggacttg gtcacatggc tgtcaagttt     600
gccaaagctc ttggagctaa tgtcacagtg attagcacat ctcctaacaa aagaaggaa     660
gccattgaga acataggagc tgactcattt gtggttagcc gtgaacaaga tcagatgcag     720
gctgtaatgg gaaccatgga tggtatcatt gacacagttt ctgctgtcca tcctcttgtg     780
cctttgattg gcctgttgaa gcctcatggt aaactagtca tggttggtgc accagagaag     840
cctttggagt tgccagtatt ttcttttactt atggggagga aaatggttgg tggcagtagc     900
atcggaggga tgaaagagac gcaagaaatg attgattttg ctgctaagca tggagtgaag     960
cctgatattg aggttattcc catagattat gtgaacactg caatagagcg cctcgccaaa    1020
gcagatgtga aatatcgatt tgtaattgac attggaaaca cgttgaagcc aagctcttga    1080
gtaaataaag aaatatgcat gcgtgattca gacttcagat actgaacgta catggggcaa    1140
gagataaaga ttgagaattg ataataattt ctttaagcat tatatgtgtt ttccgtaatg    1200
agtttttgtt tcaaggattt agctacgcta ttccttgata aataagcaat taagtgtggg    1260
gtgtgcaatt gcttaagctt ggttataatc cctttgggac gaaaattgtt ttgtactata    1320
tatacatttt aaagagtgaa attgtgtgag attatgaaca aaaaaaaaaa aaaaaaaaa    1380
aaaaaaaaa                                                            1389
```

<210> SEQ ID NO 12
<211> LENGTH: 355
<212> TYPE: PRT
<213> ORGANISM: Glycine max

<400> SEQUENCE: 12

Met Glu His Pro Lys Lys Val Phe Gly Trp Ala Ala Arg Asp Ser Ser
 1               5                  10                  15

Gly Leu Leu Ser Pro Phe Asn Phe Ser Arg Arg Glu Thr Gly Glu Lys
            20                  25                  30

Asp Leu Val Phe Lys Val Gln Tyr Cys Gly Ile Cys His Ser Asp Leu
        35                  40                  45

His Met Leu Lys Asn Glu Trp Gly Asn Thr Thr Tyr Pro Leu Val Pro
    50                  55                  60

Gly His Glu Ile Ala Gly Val Val Thr Glu Val Gly Ser Lys Val Gln
65                  70                  75                  80

Lys Phe Lys Val Gly Asp Arg Val Gly Val Gly Cys Met Ile Gly Ser

-continued

```
                    85                  90                  95
Cys Arg Ser Cys Glu Ser Cys Asp Glu Asn Leu Glu Asn Tyr Cys Pro
            100                 105                 110
Lys Met Ile Leu Thr Tyr Gly Val Lys Tyr Phe Asp Gly Thr Ile Thr
            115                 120                 125
His Gly Gly Tyr Ser Asp Leu Met Val Ala Asp Glu His Phe Val Val
            130                 135                 140
Arg Ile Pro Asp Asn Leu Pro Leu Asp Ala Ala Ala Pro Leu Leu Cys
145                 150                 155                 160
Ala Gly Ile Thr Val Tyr Ser Pro Leu Arg Tyr Tyr Gly Leu Asp Lys
                165                 170                 175
Pro Gly Leu Asn Leu Gly Val Val Gly Leu Gly Gly Leu Gly His Met
                180                 185                 190
Ala Val Lys Phe Ala Lys Ala Leu Gly Ala Asn Val Thr Val Ile Ser
                195                 200                 205
Thr Ser Pro Asn Lys Lys Glu Ala Ile Glu Asn Ile Gly Ala Asp
210                 215                 220
Ser Phe Val Val Ser Arg Glu Gln Asp Gln Met Gln Ala Val Met Gly
225                 230                 235                 240
Thr Met Asp Gly Ile Ile Asp Thr Val Ser Ala Val His Pro Leu Val
                245                 250                 255
Pro Leu Ile Gly Leu Leu Lys Pro His Gly Lys Leu Val Met Val Gly
                260                 265                 270
Ala Pro Glu Lys Pro Leu Glu Leu Pro Val Phe Ser Leu Leu Met Gly
                275                 280                 285
Arg Lys Met Val Gly Ser Ser Ile Gly Gly Met Lys Glu Thr Gln
290                 295                 300
Glu Met Ile Asp Phe Ala Ala Lys His Gly Val Lys Pro Asp Ile Glu
305                 310                 315                 320
Val Ile Pro Ile Asp Tyr Val Asn Thr Ala Ile Glu Arg Leu Ala Lys
                325                 330                 335
Ala Asp Val Lys Tyr Arg Phe Val Ile Asp Ile Gly Asn Thr Leu Lys
                340                 345                 350
Pro Ser Ser
        355
```

<210> SEQ ID NO 13
<211> LENGTH: 1418
<212> TYPE: DNA
<213> ORGANISM: Triticum aestivum

<400> SEQUENCE: 13

```
gcacgagcga acgtctaatc gcctcacaca caggaaaggc aaaaaagaaa ccaaaacctc      60
cggggagtta ctctagagat ttccggcgga acctcgcgtc aggatggcac ccacggcgac     120
ggcggcggag cagagccagc agcacacgaa gaaggcggtg gtctggcgg cgctcgacgc     180
ctccggccac ctctccccgc tcgccatcac ccgaaggagc accggagatg acgatgtcgt     240
gataaagatt ctgtactgcg ggatctgcca ctctgacctg cacagcatca agaacgactg     300
gaagaacgcc aagtacccca tgattcccgg gcacgagatc gccggcgagg tcaccgaggt     360
cggcaagaac gtgaccaagt tcaaggcagg cgaccgtgtc ggcgtcgggt gcatggtgaa     420
ctcgtgccag tcctgcgaga gctgcgacaa gggcttcgag aatcactgcc cgggcatgat     480
tttcacctac aactcggtcg accgtgacgg cacccgcacc cacggtggct actccagcat     540
```

-continued

```
ggtagtggtg cacgagcgct tcgtggtccg gtttccagac gccatgccgc tggacaaggg      600
cgcgcccctg ctgtgcgccg gcatcaccgt gtacagcccc atgaagtacc acgggctgaa      660
cgccctggg  atgcacctcg gcgtgcttgg actgggcggg ctgggccacg tcgccgtcaa      720
gttcggcaag gccttcggga tgaaggtgac cgtgatcagc tcgtcgccgg ggaagaagca      780
ggaggccctc gagaggctag cgccgacgg  gttcgttgtc agcaaggacg ccgacgagat      840
gaaggctact atgagcacca tggatggcat cataaacacg gtgtctgcaa acgtgcccat      900
ggcccctctc ttcgggctac tcaagcccaa cggcaagatg atcatggtcg gcctcccgga      960
gaagccatc  gaggtccctc cctttgctct ggttgccagg aacaagaccc tggcggggag     1020
ctgcatcggc ggcatgaggg acacccagga gatgctggac ctcgcggcga agcacggcgt     1080
gacggcagac atcgaggtga tcggcgcgga gtacgtgaac acggccatgg agcgccttgc     1140
caaggccgac gtcaggtatc gattcgtcat cgacatcgcc aacaccctcg acaaggccgc     1200
cgccgccaca accgagtgac cgccgacgta actctcagca ctactcacgg tccacgttgg     1260
tctctggttc tctgctatta tcacatactt tatctccagt agtaacaata cacagtctaa     1320
aattattgtc agtgatgtat tttttagaca aacttgtcag tgatgtatgc atggtgcgat     1380
gttgttcgac gatgggtgaa aaaaaaaaaa aaaaaaaa                             1418
```

<210> SEQ ID NO 14
<211> LENGTH: 371
<212> TYPE: PRT
<213> ORGANISM: Triticum aestivum

<400> SEQUENCE: 14

```
Met Ala Pro Thr Ala Thr Ala Glu Gln Ser Gln Gln His Thr Lys
 1               5                  10                  15

Lys Ala Val Gly Leu Ala Ala Leu Asp Ala Ser Gly His Leu Ser Pro
                20                  25                  30

Leu Ala Ile Thr Arg Arg Ser Thr Gly Asp Asp Val Val Ile Lys
             35                  40                  45

Ile Leu Tyr Cys Gly Ile Cys His Ser Asp Leu His Ser Ile Lys Asn
 50                  55                  60

Asp Trp Lys Asn Ala Lys Tyr Pro Met Ile Pro Gly His Glu Ile Ala
 65                  70                  75                  80

Gly Glu Val Thr Glu Val Gly Lys Asn Val Thr Lys Phe Lys Ala Gly
                 85                  90                  95

Asp Arg Val Gly Val Gly Cys Met Val Asn Ser Cys Gln Ser Cys Glu
            100                 105                 110

Ser Cys Asp Lys Gly Phe Glu Asn His Cys Pro Gly Met Ile Phe Thr
        115                 120                 125

Tyr Asn Ser Val Asp Arg Asp Gly Thr Arg Thr His Gly Gly Tyr Ser
    130                 135                 140

Ser Met Val Val Val His Glu Arg Phe Val Val Arg Phe Pro Asp Ala
145                 150                 155                 160

Met Pro Leu Asp Lys Gly Ala Pro Leu Leu Cys Ala Gly Ile Thr Val
                165                 170                 175

Tyr Ser Pro Met Lys Tyr His Gly Leu Asn Ala Pro Gly Met His Leu
            180                 185                 190

Gly Val Leu Gly Leu Gly Gly Leu Gly His Val Ala Val Lys Phe Gly
        195                 200                 205

Lys Ala Phe Gly Met Lys Val Thr Val Ile Ser Ser Ser Pro Gly Lys
    210                 215                 220
```

Lys Gln Glu Ala Leu Glu Arg Leu Gly Ala Asp Ala Phe Val Val Ser
225                 230                 235                 240

Lys Asp Ala Asp Glu Met Lys Ala Thr Met Ser Thr Met Asp Gly Ile
            245                 250                 255

Ile Asn Thr Val Ser Ala Asn Val Pro Met Ala Pro Leu Phe Gly Leu
            260                 265                 270

Leu Lys Pro Asn Gly Lys Met Ile Met Val Gly Leu Pro Glu Lys Pro
            275                 280                 285

Ile Glu Val Pro Pro Phe Ala Leu Val Ala Arg Asn Lys Thr Leu Ala
    290                 295                 300

Gly Ser Cys Ile Gly Gly Met Arg Asp Thr Gln Glu Met Leu Asp Leu
305                 310                 315                 320

Ala Ala Lys His Gly Val Thr Ala Asp Ile Glu Val Ile Gly Ala Glu
                325                 330                 335

Tyr Val Asn Thr Ala Met Glu Arg Leu Ala Lys Ala Asp Val Arg Tyr
            340                 345                 350

Arg Phe Val Ile Asp Ile Ala Asn Thr Leu Asp Lys Ala Ala Ala Ala
            355                 360                 365

Thr Thr Glu
    370

<210> SEQ ID NO 15
<211> LENGTH: 906
<212> TYPE: DNA
<213> ORGANISM: Zea mays
<220> FEATURE:
<221> NAME/KEY: unsure
<222> LOCATION: (817)
<220> FEATURE:
<221> NAME/KEY: unsure
<222> LOCATION: (819)
<220> FEATURE:
<221> NAME/KEY: unsure
<222> LOCATION: (857)

<400> SEQUENCE: 15
aaacaatcta cggttgccag gtctgcgacg tcagtgccga cgaactcatg gctcgcgaga      60
ggcccgtaaa aacatgatag ccagatctgc gacgtcacgg ctgtcgccag tgatcgccat     120
tcgccaccct ctccgttcca ttccaatccg ttcagcggtc agcggaacat gatacggtct     180
gcgcccttcc aagcaatcac atcttcttcc ccgttataaa tcgctcactc gctatcgtcg     240
gctacctgta tcctggcgac acccaacagc ctgcttgccg cgcttgcatt gaggggagtt     300
cggggagcgg ccggtgcgga aggaatcgac acagagttca gttcacatgg ctgctgaatc     360
agagaacggc aactgcaaag cttgggcagc gagagatcct tctggagttc tctcaccaca     420
cagttttaac cgcagagcag tgcaaagcgg cgatgtttcg ctgaagatca tatactgtgg     480
agtctgttat gcagacgttg cttggacgcg gaataagctc aatgattcaa atatcccttt     540
ggttcctggg catgagatag ctggagttgt aactcaggtt ggtgcagatg tcaaaggctt     600
taaagtgggt gaccatgtag gtgttggaac atatgtgaac tcttgccgtg attgtgagaa     660
ctgcaatatc tctctagaca accattgccc aaaagcagtt tatactttca atggcattga     720
tacagatgga actgtcacaa agggggggtta ctccactcac atttgtagtc caggaaaggt     780
attgcttcaa aatacccgat ggctaccttt ggcgaangna gcacctcttc tgtgttgctg     840
gaataccgtg tatactncaa tgatgcgaca caacatgaac caacctggaa agtcacttgg     900
ggtcat                                                                906

<210> SEQ ID NO 16
<211> LENGTH: 186
<212> TYPE: PRT
<213> ORGANISM: Zea mays
<220> FEATURE:
<221> NAME/KEY: UNSURE
<222> LOCATION: (157)..(158)
<220> FEATURE:
<221> NAME/KEY: UNSURE
<222> LOCATION: (171)

<400> SEQUENCE: 16

```
Met Ala Ala Glu Ser Glu Asn Gly Asn Cys Lys Ala Trp Ala Ala Arg
 1               5                  10                  15

Asp Pro Ser Gly Val Leu Ser Pro His Ser Phe Asn Arg Arg Ala Val
            20                  25                  30

Gln Ser Gly Asp Val Ser Leu Lys Ile Ile Tyr Cys Gly Val Cys Tyr
        35                  40                  45

Ala Asp Val Ala Trp Thr Arg Asn Lys Leu Asn Asp Ser Lys Tyr Pro
    50                  55                  60

Leu Val Pro Gly His Glu Ile Ala Gly Val Val Thr Gln Val Gly Ala
65                  70                  75                  80

Asp Val Lys Gly Phe Lys Val Gly Asp His Val Gly Val Gly Thr Tyr
                85                  90                  95

Val Asn Ser Cys Arg Asp Cys Glu Asn Cys Asn Ile Ser Leu Asp Asn
            100                 105                 110

His Cys Pro Lys Ala Val Tyr Thr Phe Asn Gly Ile Asp Thr Asp Gly
        115                 120                 125

Thr Val Thr Lys Gly Gly Tyr Ser Thr His Ile Cys Ser Pro Gly Lys
    130                 135                 140

Val Leu Leu Gln Asn Thr Arg Trp Leu Pro Leu Ala Xaa Xaa Ala Pro
145                 150                 155                 160

Leu Leu Cys Cys Trp Asn Thr Val Tyr Thr Xaa Met Met Arg His Asn
                165                 170                 175

Met Asn Gln Pro Gly Lys Ser Leu Gly Val
            180                 185
```

<210> SEQ ID NO 17
<211> LENGTH: 447
<212> TYPE: DNA
<213> ORGANISM: Oryza sativa
<220> FEATURE:
<221> NAME/KEY: unsure
<222> LOCATION: (433)

<400> SEQUENCE: 17

| | | |
|---|---|---|
| gcgccaagac gagtcgcggc tcaacagcgg agaggcggcg atctcccatc tggcgagcag | 60 |
| agcaggggag gggaagggat cttgttagag tggcatggct gctgaatgtg aagtggcaa | 120 |
| ctgtgatgct tgggcagcga gagatccttc aggatcctc tccccgtaca agttcaaccg | 180 |
| cagggctgta caaagtgacg atgtttcctt gaggatcaca cactgtggtg tttgttatgc | 240 |
| tgatgttgca tggacaagga atatactcaa caattcgatg tacccttag tccctgggca | 300 |
| tgagatagca ggagttgtaa ctgaggttgg tgcagacgtc aagagcttca agtgggtga | 360 |
| ccatgtaggt gttggcacat acgttaattc aagcccggga ctgtgagaac tgcaataact | 420 |
| ctctagagaa ctnactgctc acaacaa | 447 |

-continued

<210> SEQ ID NO 18
<211> LENGTH: 111
<212> TYPE: PRT
<213> ORGANISM: Oryza sativa

<400> SEQUENCE: 18

Met Ala Ala Glu Cys Gly Ser Gly Asn Cys Asp Ala Trp Ala Ala Arg
1               5                   10                  15
Asp Pro Ser Gly Ile Leu Ser Pro Tyr Lys Phe Asn Arg Arg Ala Val
            20                  25                  30
Gln Ser Asp Asp Val Ser Leu Arg Ile Thr His Cys Gly Val Cys Tyr
        35                  40                  45
Ala Asp Val Ala Trp Thr Arg Asn Ile Leu Asn Asn Ser Met Tyr Pro
    50                  55                  60
Leu Val Pro Gly His Glu Ile Ala Gly Val Val Thr Glu Val Gly Ala
65                  70                  75                  80
Asp Val Lys Ser Phe Lys Val Gly Asp His Val Gly Val Gly Thr Tyr
                85                  90                  95
Val Asn Ser Ser Pro Asp Cys Glu Asn Cys Asn Asn Ser Leu Glu
            100                 105                 110

<210> SEQ ID NO 19
<211> LENGTH: 1310
<212> TYPE: DNA
<213> ORGANISM: Glycine max

<400> SEQUENCE: 19

| | |
|---|---|
| gcacgagcac aagtgtgaga aaaattatga gttccaaagg tgttggtgag gattgcctgg | 60 |
| gatgggcagc aagagatgca tccggagttc tatcacctta caaattcagt cgcaggactc | 120 |
| ttgggaatga agatgttcat attaaaatta cgcactgtgg tgtttgcttc gctgatgtag | 180 |
| tttggacaag gaataaacat ggtgactcaa agtatcctgt cgtgcctggt catgagattg | 240 |
| ctgggattgt gacaaaggtt ggcgccaatg tccaccattt taaggttggc gaccatgttg | 300 |
| gagtggggac ttatatcaac tcatgtaggg attgtgagta ttgtaatgat ggacaagaag | 360 |
| ttcattgtac caagggatct gtttacactt ttaatggtgt tgattttgat ggtacaatta | 420 |
| caaaaggagg atactccagt tacatagtag tccatgagag gtactgcttc atgataccaa | 480 |
| aaagctatcc attggcttcc gcagctcctt tgctttgtgc tggaattact gtttattcac | 540 |
| cgatggtccg ccacaagatg aatcaacctg taaatctct aggagtgatt ggtcttggtg | 600 |
| gcctcggtca tatggcagtg aaatttggaa aggcatttgg tttgagtgta acggttttca | 660 |
| gcactagtat atccaagaaa gaggaggcac tgagcctgct tggtgcagac aaatttgttg | 720 |
| tttcatctaa tcaagaggaa atgacggcgt tggctaaatc gttggacttt ataatcgaca | 780 |
| cagcatctgg tgatcactcg tttgatcctt acatgtcact gctgaagaca tatggtgttt | 840 |
| ttgtcctagt tggtttccct agtcaagtca aatttatccc tgcaagcctt aatataggat | 900 |
| caaagactgt tgccggaagt gttacaggtg gtacaaaaga tatacaggag atgattggct | 960 |
| tctgtgctgc aaacgagatt cacccaaata tagaggtgat tccaatcgag tatgccaatg | 1020 |
| aagctcttga gaggctcata aatagggacg tcaagtaccg gtttgtaata gatgttgaga | 1080 |
| attccctgaa agaaaaatga gttgttgcct cccaaattgg acattattgg acttcacctt | 1140 |
| gttcgataaa taatgatggt cggagttcgt aatttactta catagagttg atttgaattt | 1200 |
| tctttaatta ttttgtgaac taatattatg tgattataag aatattttgg attttttaaat | 1260 |
| aataataatt ttgggaaaaa aaaaaaaaaa aaaaaaaaaa aaaaaaaaaa | 1310 |

<210> SEQ ID NO 20
<211> LENGTH: 357
<212> TYPE: PRT
<213> ORGANISM: Glycine max

<400> SEQUENCE: 20

Met Ser Ser Lys Gly Val Gly Glu Asp Cys Leu Gly Trp Ala Ala Arg
 1               5                  10                  15

Asp Ala Ser Gly Val Leu Ser Pro Tyr Lys Phe Ser Arg Arg Thr Leu
            20                  25                  30

Gly Asn Glu Asp Val His Ile Lys Ile Thr His Cys Gly Val Cys Phe
        35                  40                  45

Ala Asp Val Val Trp Thr Arg Asn Lys His Gly Asp Ser Lys Tyr Pro
50                  55                  60

Val Val Pro Gly His Glu Ile Ala Gly Ile Val Thr Lys Val Gly Ala
65                  70                  75                  80

Asn Val His His Phe Lys Val Gly Asp His Val Gly Val Gly Thr Tyr
                85                  90                  95

Ile Asn Ser Cys Arg Asp Cys Glu Tyr Cys Asn Asp Gly Gln Glu Val
            100                 105                 110

His Cys Thr Lys Gly Ser Val Tyr Thr Phe Asn Gly Val Asp Phe Asp
        115                 120                 125

Gly Thr Ile Thr Lys Gly Gly Tyr Ser Ser Tyr Ile Val Val His Glu
130                 135                 140

Arg Tyr Cys Phe Met Ile Pro Lys Ser Tyr Pro Leu Ala Ser Ala Ala
145                 150                 155                 160

Pro Leu Leu Cys Ala Gly Ile Thr Val Tyr Ser Pro Met Val Arg His
                165                 170                 175

Lys Met Asn Gln Pro Gly Lys Ser Leu Gly Val Ile Gly Leu Gly Gly
            180                 185                 190

Leu Gly His Met Ala Val Lys Phe Gly Lys Ala Phe Gly Leu Ser Val
        195                 200                 205

Thr Val Phe Ser Thr Ser Ile Ser Lys Lys Glu Ala Leu Ser Leu
210                 215                 220

Leu Gly Ala Asp Lys Phe Val Val Ser Ser Asn Gln Glu Glu Met Thr
225                 230                 235                 240

Ala Leu Ala Lys Ser Leu Asp Phe Ile Ile Asp Thr Ala Ser Gly Asp
                245                 250                 255

His Ser Phe Asp Pro Tyr Met Ser Leu Leu Lys Thr Tyr Gly Val Phe
            260                 265                 270

Val Leu Val Gly Phe Pro Ser Gln Val Lys Phe Ile Pro Ala Ser Leu
        275                 280                 285

Asn Ile Gly Ser Lys Thr Val Ala Gly Ser Val Thr Gly Gly Thr Lys
290                 295                 300

Asp Ile Gln Glu Met Ile Gly Phe Cys Ala Ala Asn Glu Ile His Pro
305                 310                 315                 320

Asn Ile Glu Val Ile Pro Ile Glu Tyr Ala Asn Glu Ala Leu Glu Arg
                325                 330                 335

Leu Ile Asn Arg Asp Val Lys Tyr Arg Phe Val Ile Asp Val Glu Asn
            340                 345                 350

Ser Leu Lys Glu Lys
        355

```
<210> SEQ ID NO 21
<211> LENGTH: 615
<212> TYPE: DNA
<213> ORGANISM: Triticum aestivum
<220> FEATURE:
<221> NAME/KEY: unsure
<222> LOCATION: (463)
<220> FEATURE:
<221> NAME/KEY: unsure
<222> LOCATION: (487)
<220> FEATURE:
<221> NAME/KEY: unsure
<222> LOCATION: (505)
<220> FEATURE:
<221> NAME/KEY: unsure
<222> LOCATION: (516)
<220> FEATURE:
<221> NAME/KEY: unsure
<222> LOCATION: (574)
<220> FEATURE:
<221> NAME/KEY: unsure
<222> LOCATION: (589)
<220> FEATURE:
<221> NAME/KEY: unsure
<222> LOCATION: (596)
<220> FEATURE:
<221> NAME/KEY: unsure
<222> LOCATION: (604)
<220> FEATURE:
<221> NAME/KEY: unsure
<222> LOCATION: (607)

<400> SEQUENCE: 21
gtttcccgtt tgataccgca ccgctgtagc tggagtacat agtagctgac gtcaatgccc      60
tacacacgta gtgtctgacg ttcgatccaa ctcgtcagct cgcctattta tccccaacct    120
cgtggcctgg cagtgtcatc cggatatttt tgagcaggaa atcgaagtgc caggaccgaa    180
gaagcagagc aagcagtcat caatggcgaa aggcacgcct gcgaccggtt gggccgcgaa    240
ggacccgtcc ggtgtcctct cccctacag cttctcacga agggctctga aggacgacga    300
tgtcaccatc aaggtgctct ctgcggatt ctgccacacc gacctccaca tcgccaagaa    360
cgagtgggga aacgccctct acccgtcgtc cccggggcat gagattgttg cgtcctcac    420 cgacgctggg cccggcgtca agaattcaa ggccggggac acngtgggcg tgggctactt    480
cgtcgantcc tgccgctcct gcgtnaactg cggcancggg cacaagaaca ctgcccaagc    540
tcgtgctcac tccaacgccg tggactacga cgggnccaca accaaggang gtctcnaagt    600
ctcntcntca caagg                                                     615

<210> SEQ ID NO 22
<211> LENGTH: 103
<212> TYPE: PRT
<213> ORGANISM: Triticum aestivum
<220> FEATURE:
<221> NAME/KEY: UNSURE
<222> LOCATION: (95)

<400> SEQUENCE: 22

Met Ala Lys Gly Thr Pro Ala Thr Gly Trp Ala Ala Lys Asp Pro Ser
 1               5                  10                  15

Gly Val Leu Ser Pro Tyr Ser Phe Ser Arg Arg Ala Leu Lys Asp Asp
                20                  25                  30

Asp Val Thr Ile Lys Val Leu Phe Cys Gly Phe Cys His Thr Asp Leu
            35                  40                  45

His Ile Ala Lys Asn Glu Trp Gly Asn Ala Leu Tyr Pro Ser Ser Pro
        50                  55                  60
```

```
Gly His Glu Ile Val Gly Val Leu Thr Asp Ala Gly Pro Gly Val Lys
 65                  70                  75                  80

Glu Phe Lys Ala Gly Asp Thr Val Gly Val Gly Tyr Phe Val Xaa Ser
                 85                  90                  95

Cys Arg Ser Cys Val Asn Cys
            100
```

<210> SEQ ID NO 23
<211> LENGTH: 453
<212> TYPE: DNA
<213> ORGANISM: Triticum aestivum

<400> SEQUENCE: 23

```
ctcgtgccga attcggcacg aggtacccct tagtccctgg gcatgagatt gctggagttg    60
taaccgaggt tggttcagac gtcaagggct caaactggg cgaccatgtg gctgttggga    120
catatgtcaa ctcatgccgt gactgtgaca actgcaatag cttcctcgat aaccactgct   180
caaagtttgt tttcactttc aatggtgttg atactgacgg tactgtcaca aagggaggat   240
attccagtca cattgttgtt catgaacggt attgctataa aatacctgat ggctacccac   300
tggaaaaggc cgcaccttta gtttgtgctg ggatcactgt gtacagtccg atgatgcgac   360
ataacatgaa ccagccagga agtcactcg gtgtcattgg tctcggtggg ttgggtcaca   420
tggcagtgaa atttgggaaa gcctttggac tga                                453
```

<210> SEQ ID NO 24
<211> LENGTH: 150
<212> TYPE: PRT
<213> ORGANISM: Triticum aestivum

<400> SEQUENCE: 24

```
Arg Ala Glu Phe Gly Thr Arg Tyr Pro Leu Val Pro Gly His Glu Ile
  1               5                  10                  15

Ala Gly Val Val Thr Glu Val Gly Ser Asp Val Lys Gly Phe Lys Leu
                 20                  25                  30

Gly Asp His Val Ala Val Gly Thr Tyr Val Asn Ser Cys Arg Asp Cys
             35                  40                  45

Asp Asn Cys Asn Ser Phe Leu Asp Asn His Cys Ser Lys Phe Val Phe
         50                  55                  60

Thr Phe Asn Gly Val Asp Thr Asp Gly Thr Val Thr Lys Gly Gly Tyr
 65                  70                  75                  80

Ser Ser His Ile Val Val His Glu Arg Tyr Cys Tyr Lys Ile Pro Asp
                 85                  90                  95

Gly Tyr Pro Leu Glu Lys Ala Ala Pro Leu Val Cys Ala Gly Ile Thr
            100                 105                 110

Val Tyr Ser Pro Met Met Arg His Asn Met Asn Gln Pro Gly Lys Ser
        115                 120                 125

Leu Gly Val Ile Gly Leu Gly Leu Gly His Met Ala Val Lys Phe
    130                 135                 140

Gly Lys Ala Phe Gly Leu
145                 150
```

<210> SEQ ID NO 25
<211> LENGTH: 458
<212> TYPE: DNA
<213> ORGANISM: Zea mays

<400> SEQUENCE: 25

```
gacctctcaa atcattcaat tccccagtac tgccactcgt ggtgtattca agcaaaccac    60
gatcgaaaca cctgcacttg ccaacaatga agtgctgatc aagatcctcg ctagcggtgt   120
ctgtcacaca gactgtggct tcatgggtca agatggcctt gtccttggtc atgaatccgt   180
gggccgtgtt gttcagatcg gatccgatgt caaaaagatt caagtgggtg atgtggttgg   240
tagttcctat ttgaaggaat cctgtttgag ctgtccctct tgtaattcgg gtgtagatac   300
caattgtgat aatagaaaga tgttccctga aggaaactca aatggattcg cctctcatca   360
aatcgctgac agtcgctttg tctacaagat tcctgatcat ttagaaccca agcatgctgg   420
tcccttgatg tgtgctggta tcactgtctt taatgctc                           458
```

<210> SEQ ID NO 26
<211> LENGTH: 152
<212> TYPE: PRT
<213> ORGANISM: Zea mays

<400> SEQUENCE: 26

```
Thr Ser Gln Ile Ile Gln Phe Pro Ser Thr Ala Thr Arg Gly Val Phe
 1               5                  10                  15

Lys Gln Thr Thr Ile Glu Thr Pro Ala Leu Ala Asn Asn Glu Val Leu
            20                  25                  30

Ile Lys Ile Leu Ala Ser Gly Val Cys His Thr Asp Cys Gly Phe Met
        35                  40                  45

Gly Gln Asp Gly Leu Val Leu Gly His Glu Ser Val Gly Arg Val Val
    50                  55                  60

Gln Ile Gly Ser Asp Val Lys Lys Ile Gln Val Gly Asp Val Val Gly
65                  70                  75                  80

Ser Ser Tyr Leu Lys Glu Ser Cys Leu Ser Cys Pro Ser Cys Asn Ser
                85                  90                  95

Gly Val Asp Thr Asn Cys Asp Asn Arg Lys Met Phe Pro Glu Gly Asn
            100                 105                 110

Ser Asn Gly Phe Ala Ser His Gln Ile Ala Asp Ser Arg Phe Val Tyr
        115                 120                 125

Lys Ile Pro Asp His Leu Glu Pro Lys His Ala Gly Pro Leu Met Cys
    130                 135                 140

Ala Gly Ile Thr Val Phe Asn Ala
145                 150
```

<210> SEQ ID NO 27
<211> LENGTH: 1023
<212> TYPE: DNA
<213> ORGANISM: Glycine max
<220> FEATURE:
<221> NAME/KEY: unsure
<222> LOCATION: (103)
<220> FEATURE:
<221> NAME/KEY: unsure
<222> LOCATION: (111)
<220> FEATURE:
<221> NAME/KEY: unsure
<222> LOCATION: (118)

<400> SEQUENCE: 27

```
catcactcta ccacctagca tctctctaac tttgagaaag tgtgtgttgt gtgttctctt    60
ctctcactaa aaaaggtttc attaattcta tattatggct canaccacag ngaatcanac   120
agtgaccgta tctgggtggg cagctcatga ttcttcgggc aagattaccc cctacacttt   180
caaaagaagg ggagaatggt gtgaacgatg tgacaataaa gatactgtat tgtgggatct   240
```

-continued

```
gccacacgga cctccactat gctaaaaatg aatggggcat tactatgtat cctgtagtac    300
ccggacacga gatcattggg gtggtaacta aggtggggag agacgtgaag gggttcaagg    360
aaggagacag agtgggtgtg gggtgtttgg cggcttcatg tttggaatgt gagcactgca    420
agaccgatca ggaaaattac tgtgaaaagt tgcaatttgt ctacaacgga gtattctggg    480
atggcagcat cacctatggg ggctactctc aaattttgt cgcagattac agatatgtgg     540
tacacattcc ggaaaaccta gcaatggatg cagcggctcc tctgctatgc gcaggaataa    600
cagtgttcaa tcctttgaaa gaccacgatt tggtagcatc accgggaaag aagattgggg    660
tggttggtct gggaggcctt gggcacattg ccgttaaatt tggcaaggct ttcggccacc    720
atgttaccgt catcagcact tctccctcca aggaggctga agctaagcag cgtttgggtg    780
ctgatgattt cattgtcagc tccaacccta acaattaca ggctgcaagg agaagcatag     840
atttcatatt ggacactgtt tcggcagagc actctctgtt gcccatcttg gaattgctca    900
aagtcaacgg gaccttattt ctcgtgggtg caccaagaca aagcccttac aattgccagc    960
tttcccattg atatttggca agagatcagt gaaaggtggg atcatagggg gaataaaaga   1020
gac                                                                 1023
```

<210> SEQ ID NO 28
<211> LENGTH: 292
<212> TYPE: PRT
<213> ORGANISM: Glycine max
<220> FEATURE:
<221> NAME/KEY: UNSURE
<222> LOCATION: (264)

<400> SEQUENCE: 28

```
Met Ile Leu Arg Ala Arg Leu Pro Pro Thr Leu Ser Lys Glu Gly Glu
  1               5                  10                  15

Asn Gly Val Asn Asp Val Thr Ile Lys Ile Leu Tyr Cys Gly Ile Cys
             20                  25                  30

His Thr Asp Leu His Tyr Ala Lys Asn Glu Trp Gly Ile Thr Met Tyr
         35                  40                  45

Pro Val Pro Gly His Glu Ile Ile Gly Val Thr Lys Val Gly
     50                  55                  60

Arg Asp Val Lys Gly Phe Lys Glu Gly Asp Arg Val Gly Val Gly Cys
 65                  70                  75                  80

Leu Ala Ala Ser Cys Leu Glu Cys Glu His Cys Lys Thr Asp Gln Glu
                 85                  90                  95

Asn Tyr Cys Glu Lys Leu Gln Phe Val Tyr Asn Gly Val Phe Trp Asp
            100                 105                 110

Gly Ser Ile Thr Tyr Gly Gly Tyr Ser Gln Ile Phe Val Ala Asp Tyr
        115                 120                 125

Arg Tyr Val Val His Ile Pro Glu Asn Leu Ala Met Asp Ala Ala Ala
130                 135                 140

Pro Leu Leu Cys Ala Gly Ile Thr Val Phe Asn Pro Leu Lys Asp His
145                 150                 155                 160

Asp Leu Val Ala Ser Pro Gly Lys Lys Ile Gly Val Val Gly Leu Gly
                165                 170                 175

Gly Leu Gly His Ile Ala Val Lys Phe Gly Lys Ala Phe Gly His His
            180                 185                 190

Val Thr Val Ile Ser Thr Ser Pro Ser Lys Glu Ala Glu Ala Lys Gln
        195                 200                 205

Arg Leu Gly Ala Asp Asp Phe Ile Val Ser Ser Asn Pro Lys Gln Leu
```

```
                210                 215                 220
Gln Ala Ala Arg Arg Ser Ile Asp Phe Ile Leu Asp Thr Val Ser Ala
225                 230                 235                 240

Glu His Ser Leu Leu Pro Ile Leu Glu Leu Leu Lys Val Asn Gly Thr
                245                 250                 255

Leu Phe Leu Val Gly Ala Pro Xaa Thr Lys Pro Leu Gln Leu Pro Ala
            260                 265                 270

Phe Pro Leu Ile Phe Gly Lys Arg Ser Val Lys Gly Ile Ile Gly
        275                 280                 285

Gly Ile Lys Glu
    290

<210> SEQ ID NO 29
<211> LENGTH: 1171
<212> TYPE: DNA
<213> ORGANISM: Glycine max
<220> FEATURE:
<221> NAME/KEY: unsure
<222> LOCATION: (3)
<220> FEATURE:
<221> NAME/KEY: unsure
<222> LOCATION: (685)

<400> SEQUENCE: 29 aanccttta  gcaagttaac  aacactttg   tcttcgttcc  attatctagt  tctcaattct    60
cttcacccct  tgcctctgaa  agaaatgggt  agtcttgaag  cggaaagaac  aacagtagga   120
ttggcagcaa  gagacccttc  agggattctc  tccccataca  cctacaatct  aagaaacaca   180
ggccctgatg  atgtttacat  taaagttcac  tactgtggaa  tttgccattc  tgatctccac   240
cagattaaaa  atgatcttgg  catgtccaac  tatcccatgg  tcccaggaca  tgaagtggtt   300
ggtgaggtac  tggaggtggg  atcaaacgtt  agcaggttca  gagtgggaga  gttggtggga   360
gttggactcc  tcgtaggttg  ctgcaaaaac  tgccagccat  gccaacaaga  cattgagaat   420
tactgcagca  agaagatctg  gtcttacaat  gatgtttatg  tcgatggaaa  acccacacag   480
ggtggctttg  ctgaaaccat  gatcgttgag  caaaagtttg  tggtgaagat  tccagagggt   540
ttggcgccag  agcaagtggc  accattactg  tgtgcgggtg  tgacagtgta  cagtccactg   600
gtacactttg  ggctgaaaga  gagtgggcta  agaggtggaa  tattggggct  tggaggagtg   660
ggacacatgg  gggtgaagat  agcanaggca  ctgggtcatc  atgtgactgt  gataagctct   720
tctgacaaga  agaaacaaga  ggcacttgaa  caccttggag  ctgatcaata  tctcgttagc   780
tctgatgcca  ctgccatgca  ggaagctgct  gattcacttg  actacatcat  tgacactgtg   840
cctgttggtc  accctcttga  gccttatctc  tccttgctca  aacttgatgg  caagttgatc   900
ttgatggggg  tcatcaacac  ccctcttcaa  tttgttagcc  ccatggtcat  gctagggagg   960
aagtcaataa  cgggaagctt  cattgggagc  atgaaggaga  cagaggagat  gttggagttc  1020
tggaaagaga  agggtctgag  ttcgatgatt  gaaatggtaa  acatggatta  cattaacaaa  1080
gcctttgaaa  ggttggagaa  gaatgacgtg  agatacaggt  ttgttgtgga  tgtcaaaggc  1140
agcaaacttg  tcgatcagta  aaagaaagaa  a                                   1171

<210> SEQ ID NO 30
<211> LENGTH: 358
<212> TYPE: PRT
<213> ORGANISM: Glycine max
<220> FEATURE:
<221> NAME/KEY: UNSURE
<222> LOCATION: (201)
```

<400> SEQUENCE: 30

```
Met Gly Ser Leu Glu Ala Glu Arg Thr Thr Val Gly Leu Ala Ala Arg
 1               5                  10                  15

Asp Pro Ser Gly Ile Leu Ser Pro Tyr Thr Tyr Asn Leu Arg Asn Thr
             20                  25                  30

Gly Pro Asp Asp Val Tyr Ile Lys Val His Tyr Cys Gly Ile Cys His
         35                  40                  45

Ser Asp Leu His Gln Ile Lys Asn Asp Leu Gly Met Ser Asn Tyr Pro
 50                  55                  60

Met Val Pro Gly His Glu Val Val Gly Glu Val Leu Glu Val Gly Ser
 65                  70                  75                  80

Asn Val Ser Arg Phe Arg Val Gly Glu Leu Val Gly Val Gly Leu Leu
                 85                  90                  95

Val Gly Cys Cys Lys Asn Cys Gln Pro Cys Gln Gln Asp Ile Glu Asn
            100                 105                 110

Tyr Cys Ser Lys Lys Ile Trp Ser Tyr Asn Asp Val Tyr Val Asp Gly
            115                 120                 125

Lys Pro Thr Gln Gly Gly Phe Ala Glu Thr Met Ile Val Glu Gln Lys
130                 135                 140

Phe Val Lys Ile Pro Glu Gly Leu Ala Pro Glu Gln Val Ala Pro
145                 150                 155                 160

Leu Leu Cys Ala Gly Val Thr Val Tyr Ser Pro Leu Val His Phe Gly
                165                 170                 175

Leu Lys Glu Ser Gly Leu Arg Gly Gly Ile Leu Gly Leu Gly Gly Val
            180                 185                 190

Gly His Met Gly Val Lys Ile Ala Xaa Ala Leu Gly His His Val Thr
        195                 200                 205

Val Ile Ser Ser Ser Asp Lys Lys Gln Glu Ala Leu Glu His Leu
    210                 215                 220

Gly Ala Asp Gln Tyr Leu Val Ser Ser Asp Ala Thr Ala Met Gln Glu
225                 230                 235                 240

Ala Ala Asp Ser Leu Asp Tyr Ile Ile Asp Thr Val Pro Val Gly His
                245                 250                 255

Pro Leu Glu Pro Tyr Leu Ser Leu Leu Lys Leu Asp Gly Lys Leu Ile
            260                 265                 270

Leu Met Gly Val Ile Asn Thr Pro Leu Gln Phe Val Ser Pro Met Val
        275                 280                 285

Met Leu Gly Arg Lys Ser Ile Thr Gly Ser Phe Ile Gly Ser Met Lys
    290                 295                 300

Glu Thr Glu Glu Met Leu Glu Phe Trp Lys Lys Gly Leu Ser Ser
305                 310                 315                 320

Met Ile Glu Met Val Asn Met Asp Tyr Ile Asn Lys Ala Phe Glu Arg
                325                 330                 335

Leu Glu Lys Asn Asp Val Arg Tyr Arg Phe Val Val Asp Val Lys Gly
            340                 345                 350

Ser Lys Leu Val Asp Gln
        355
```

<210> SEQ ID NO 31
<211> LENGTH: 1308
<212> TYPE: DNA
<213> ORGANISM: Triticum aestivum

<400> SEQUENCE: 31

```
gcaaaggcaa gtgcaagtcc tcccaaatcc acgcatccct cgcccgcgtc tcctcccgtt      60
gccgcagcag caagagaatg ggcagcgtcg acgcctccga cgacggtc accgggtggg      120
ccgccaggga cgccaccggc cacctctccc cctacagata caccctcagg aaaacaggac    180
ctgaagacgt ggtgttgaag gttaagtact gcggcatctg ccacactgac gtccaccagg    240
tcaagaacga cctcggtgct tcgaagtacc ccatggtccc agggcatgag gtggttggcg    300
aggtggtgga ggtcgggccg gaggtgagca gttccgggc cggcgacgtg gtgggcgtgg     360
gggtgatcgt ggggtgctgc cgcgactgcc ggccgtgcaa ggccaacgtc gagcagtact    420
gcaacaagaa gatctggtcg tacaacgacg tctacaccga cggcaagccg acgcagggcg    480
gcttcgcctc cgccatggtc gtcgatcaga agttcgtggt gaagatcccc gccgggctgg    540
cgccggagca ggcggcgccg ctgctgtgcg cggggggtgac ggtgtacagc ccgctgaagc   600
acttcgggct catgaccccg ggcctccgcg gcgggatact gggcctgggc ggcgtgggcc    660
acatgggcgt gaaggtggcc aagtccatgg gccaccacgt gacggtgatc agctcgtcca   720
acaagaagcg ggccgaggcc atggacgacc tgggcgccga cgcgtacctc gtcagctccg    780
acaccgacca gatggccgcc gccgccgact cgctggacta catcatcgac accgtgcccg    840
ccaagcaccc gctggagccc tacctggcgc tgctcaagat ggacggcaag ctggtgctga    900
tgggcgtgat cgcggagccg ctcagcttcg tgtcccccat ggtgatgctg ggaggaaga     960
ccatcacggg gagcttcatc gggagcatgg acgagacgga ggaggtgctc cagttctgcg   1020
tcgacaaagg gctcacctcg cagatcgagg tcgtcaagat ggactacgtc aaccaggcgt   1080
tcgagaggct cgagcgcaac gacgtccgct accgcttcgt cgtcgacgtc ggcgggagca   1140
acatcgagga cgccgcctga tcgatgacgg ccgggaaaaa gagagagcta gaccgagcgg   1200
cgagtgcaat gacagtatca tgtgtgcccg tgccatttgc ctgtacttga tgcagtacat   1260
ttcgtgacct gttccgtttt catcaaattc gcgcgttcgt ttcggtgg              1308
```

<210> SEQ ID NO 32
<211> LENGTH: 360
<212> TYPE: PRT
<213> ORGANISM: Triticum aestivum

<400> SEQUENCE: 32

```
Met Gly Ser Val Asp Ala Ser Glu Thr Thr Val Thr Gly Trp Ala Ala
 1               5                  10                  15

Arg Asp Ala Thr Gly His Leu Ser Pro Tyr Arg Tyr Thr Leu Arg Lys
            20                  25                  30

Thr Gly Pro Glu Asp Val Val Leu Lys Val Lys Tyr Cys Gly Ile Cys
        35                  40                  45

His Thr Asp Val His Gln Val Lys Asn Asp Leu Gly Ala Ser Lys Tyr
    50                  55                  60

Pro Met Val Pro Gly His Glu Val Val Gly Val Val Glu Val Gly
65                  70                  75                  80

Pro Glu Val Ser Lys Phe Arg Ala Gly Asp Val Val Gly Val Gly Val
                85                  90                  95

Ile Val Gly Cys Cys Arg Asp Cys Arg Pro Cys Lys Ala Asn Val Glu
            100                 105                 110

Gln Tyr Cys Asn Lys Lys Ile Trp Ser Tyr Asn Asp Val Tyr Thr Asp
        115                 120                 125

Gly Lys Pro Thr Gln Gly Gly Phe Ala Ser Ala Met Val Val Asp Gln
    130                 135                 140
```

```
Lys Phe Val Val Lys Ile Pro Ala Gly Leu Ala Pro Glu Gln Ala Ala
145                 150                 155                 160

Pro Leu Leu Cys Ala Gly Val Thr Val Tyr Ser Pro Leu Lys His Phe
            165                 170                 175

Gly Leu Met Thr Pro Gly Leu Arg Gly Ile Leu Gly Leu Gly Gly
        180                 185                 190

Val Gly His Met Gly Val Lys Val Ala Lys Ser Met Gly His His Val
        195                 200                 205

Thr Val Ile Ser Ser Ser Asn Lys Lys Arg Ala Glu Ala Met Asp Asp
        210                 215                 220

Leu Gly Ala Asp Ala Tyr Leu Val Ser Ser Asp Thr Asp Gln Met Ala
225                 230                 235                 240

Ala Ala Ala Asp Ser Leu Asp Tyr Ile Ile Asp Thr Val Pro Ala Lys
                245                 250                 255

His Pro Leu Glu Pro Tyr Leu Ala Leu Leu Lys Met Asp Gly Lys Leu
            260                 265                 270

Val Leu Met Gly Val Ile Ala Glu Pro Leu Ser Phe Val Ser Pro Met
        275                 280                 285

Val Met Leu Gly Arg Lys Thr Ile Thr Gly Ser Phe Ile Gly Ser Met
        290                 295                 300

Asp Glu Thr Glu Glu Val Leu Gln Phe Cys Val Asp Lys Gly Leu Thr
305                 310                 315                 320

Ser Gln Ile Glu Val Val Lys Met Asp Tyr Val Asn Gln Ala Phe Glu
            325                 330                 335

Arg Leu Glu Arg Asn Asp Val Arg Tyr Arg Phe Val Val Asp Val Gly
            340                 345                 350 ly Ser Asn Ile Glu Asp Ala Ala
        355                 360

<210> SEQ ID NO 33
<211> LENGTH: 1347
<212> TYPE: DNA
<213> ORGANISM: Glycine max

<400> SEQUENCE: 33
gcacgagatt tatacttgag aaatcccttt cacttcttcc tctcttcttc ttctatttcc     60
tcataccatt actcccatca tctatctgaa ctctcacact tctccgttca gaaatctcaa    120
catataatca tattacttac ccctccaaac ctacccctcc atcaccccca taataaaacc    180
aaaatgggat atcccgagac ctttacagga ttccaaattg aagatcctgc aaaatggacc    240
gagtttcata agaaccaata tacacctaag ccattcggcg actttgatgt cgatatcaag    300
attttggcct gtggtgtttg cgcgagtgat ttgcatactg ttagtggagg gtggggtgaa    360
cagaagtttc gctttgtgt gggcatgaa attgtaggag aagccctccg cgtcggccca    420
aaagtaactc tcatcaagcc cggtcaacgt gttggtgttg gtgctcaatc atactcctgt    480
ctccaatgtc gtcagtgcaa aaatgacaac gagacatact gtcttcacca actcgatacc    540
tatggagccg tctggcccga aacgggtatc gtttcccaag gtggctatgc tagccatgtg    600
agaactcatg agcattgggt tttccccatt ccagatggat tgaagaccga agaggcggct    660
cctatgttgt gtgctggttt gacggcttat agtccttttgg ttagaaatgg ctgtggacct    720
ggaaagaagg tgggtattgt gggattggga ggaattggtc atttggtgt tatgtttgct    780 aaggctttgg gcgctgagac ttgggctatt tcgagaaccc acgccaaaga agccgatgca    840
```

```
aagaaactcg gcgctgatgg ctttctcgcc acagccgaca aggactggaa caaagagcac    900
atcatgccct tcgacttgat agtcaacaca gcttcttcct cctcaggatt caatttctcc    960
gagtacctcg agctcctcga cgtacacggc cactgggtat ccgtcggact ccccgaaggc   1020
gaaggtcaaa cgatcgataa ctttcaacta ttgaaaaacg tgttctcat cggaggaagt    1080 catctaggta gcagaaaaga ggttctggcc atgttggatt tagccgtgga aagggtatc    1140 aatagttggg ttgagacgat tgatattagt gaggagggat tgaagacggc cttgacgagg   1200
ttgcataata atgatgttag gtatagattt acgatggtgg gttatgagaa gtgttttggt   1260
acttagaatg ggttattact cgtttgtaag attttatgta ggcgagatag taagctttac   1320
atctttacca aaaaaaaaaa aaaaaaa                                       1347
```

<210> SEQ ID NO 34
<211> LENGTH: 360
<212> TYPE: PRT
<213> ORGANISM: Glycine max

<400> SEQUENCE: 34

```
Met Gly Tyr Pro Glu Thr Phe Thr Gly Phe Gln Ile Glu Asp Pro Ala
 1               5                  10                  15

Lys Trp Thr Glu Phe His Lys Asn Gln Tyr Thr Pro Lys Pro Phe Gly
            20                  25                  30

Asp Phe Asp Val Asp Ile Lys Ile Leu Ala Cys Gly Val Cys Ala Ser
        35                  40                  45

Asp Leu His Thr Val Ser Gly Gly Trp Gly Glu Gln Lys Phe Pro Leu
    50                  55                  60

Cys Val Gly His Glu Ile Val Gly Glu Ala Leu Arg Val Gly Pro Lys
65                  70                  75                  80

Val Thr Leu Ile Lys Pro Gly Gln Arg Val Gly Val Gly Ala Gln Ser
                85                  90                  95

Tyr Ser Cys Leu Gln Cys Arg Gln Cys Lys Asn Asp Asn Glu Thr Tyr
            100                 105                 110

Cys Leu His Gln Leu Asp Thr Tyr Gly Ala Val Trp Pro Glu Thr Gly
        115                 120                 125

Ile Val Ser Gln Gly Gly Tyr Ala Ser His Val Arg Thr His Glu His
    130                 135                 140

Trp Val Phe Pro Ile Pro Asp Gly Leu Lys Thr Glu Glu Ala Ala Pro
145                 150                 155                 160

Met Leu Cys Ala Gly Leu Thr Ala Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

His Phe Gly Val Met Phe Ala Lys Ala Leu Gly Ala Glu Thr Trp Ala
        195                 200                 205

Ile Ser Arg Thr His Ala Lys Glu Ala Asp Ala Lys Lys Leu Gly Ala
    210                 215                 220

Asp Gly Phe Leu Ala Thr Ala Asp Lys Asp Trp Asn Lys Glu His Ile
225                 230                 235                 240

Met Pro Phe Asp Leu Ile Val Asn Thr Ala Ser Ser Ser Gly Phe
                245                 250                 255

Asn Phe Ser Glu Tyr Leu Glu Leu Leu Asp Val His Gly His Trp Val
            260                 265                 270

Ser Val Gly Leu Pro Glu Gly Glu Gly Gln Thr Ile Asp Asn Phe Gln
        275                 280                 285
```

```
Leu Leu Lys Asn Gly Val Leu Ile Gly Gly Ser His Leu Gly Ser Arg
        290                 295                 300

Lys Glu Val Leu Ala Met Leu Asp Leu Ala Val Glu Lys Gly Ile Asn
305                 310                 315                 320

Ser Trp Val Glu Thr Ile Asp Ile Ser Glu Glu Gly Leu Lys Thr Ala
                325                 330                 335

Leu Thr Arg Leu His Asn Asn Asp Val Arg Tyr Arg Phe Thr Met Val
            340                 345                 350

Gly Tyr Glu Lys Cys Phe Gly Thr
        355                 360

<210> SEQ ID NO 35
<211> LENGTH: 767
<212> TYPE: DNA
<213> ORGANISM: Oryza sativa
<220> FEATURE:
<221> NAME/KEY: unsure
<222> LOCATION: (30)
<220> FEATURE:
<221> NAME/KEY: unsure
<222> LOCATION: (135)
<220> FEATURE:
<221> NAME/KEY: unsure
<222> LOCATION: (744)
<220> FEATURE:
<221> NAME/KEY: unsure
<222> LOCATION: (747)

<400> SEQUENCE: 35
gttctaaccg ccggcgagaa acctgcagan ggcgagggcg agtgcggcgg acagggatg       60 gaggagcatg gcaaggcggc tgtcggctgg gcggccaggg acgactccgg cgtcctctcc     120
ccgtacaact tctcnaggag ggctcagaag gacgatgacg tcaccatcaa ggtgctctac     180
tgcggcatct gccacactga cctgcacatc gtcaagaatg attggggcaa cgccatgtac     240
cccgtcgtcc ccggccacga gatcgtcggc gtcgtcaccg gcgtcggcgc cggcgtgacc     300
aagttcaagg ccggcgacac ggtgggcgtg ggctacttcg tcgcgtcgtg ccgcggctgc     360
gagtgctgcg ggaatgggta cgagaactac tgcgccaaga tggtaaccac ctgcaacggc     420
gtcgaccacg accacggcgg cggcgcggcc acccagggcg gcttctccga cgccatcgtc     480
gtcaacgagc actacgtgct ccgcgtgccg gcggggctgc cgctggacag cgcggcgccg     540
ctgctgtgcg ccggcgtgac ggtgtacagc ccgatggtga tccacggcct gaacccccgg     600
ggaacactcg gcgtctcggc tcggcggctc ggcactccct caattcgcca agcttcggga     660
tcgctcacct ctcacactcc cggggaagcg caggaggact ggacactcgg gccacgattc     720
tctcagcgag agcggcaaat gcgnggngcg gcacaaggcg gatctaa                   767

<210> SEQ ID NO 36
<211> LENGTH: 125
<212> TYPE: PRT
<213> ORGANISM: Oryza sativa

<400> SEQUENCE: 36

Met Glu Glu His Gly Lys Ala Ala Val Gly Trp Ala Ala Arg Asp Asp
1               5                   10                  15

Ser Gly Val Leu Ser Pro Tyr Asn Phe Ser Arg Arg Ala Gln Lys Asp
            20                  25                  30

Asp Asp Val Thr Ile Lys Val Leu Tyr Cys Gly Ile Cys His Thr Asp
        35                  40                  45
```

```
Leu His Ile Val Lys Asn Asp Trp Gly Asn Ala Met Tyr Pro Val Val
 50                  55                  60

Pro Gly His Glu Ile Val Gly Val Val Thr Gly Val Gly Ala Gly Val
 65                  70                  75                  80

Thr Lys Phe Lys Ala Gly Asp Thr Val Gly Val Gly Tyr Phe Val Ala
                 85                  90                  95

Ser Cys Arg Gly Cys Glu Cys Cys Gly Asn Gly Tyr Glu Asn Tyr Cys
            100                 105                 110

Ala Lys Met Val Thr Thr Cys Asn Gly Val Asp His Asp
            115                 120                 125
```

<210> SEQ ID NO 37
<211> LENGTH: 577
<212> TYPE: DNA
<213> ORGANISM: Triticum aestivum
<220> FEATURE:
<221> NAME/KEY: unsure
<222> LOCATION: (475)
<220> FEATURE:
<221> NAME/KEY: unsure
<222> LOCATION: (530)
<220> FEATURE:
<221> NAME/KEY: unsure
<222> LOCATION: (557)
<220> FEATURE:
<221> NAME/KEY: unsure
<222> LOCATION: (564)
<220> FEATURE:
<221> NAME/KEY: unsure
<222> LOCATION: (571)

<400> SEQUENCE: 37

```
tcgtggttag tgattacgac cagcaagtca caagtgaggg cgggagaggt tgaggttgag    60
gaagagcaga ggaatccatt ccaggagtgt ttaatggcgg gaggcaagga agcgcacggg   120
tgggcagcca gggatgtctc tggtcacctc tccccttacc acttctcacg gagggttcag   180
agagacgacg acgtcaccat caaggtgctc ttctgcgggc tttgccacac tgacctccac   240
gtcatcaaga acgagtttgg caacgccaag tacccccgtcg ttcccgggca cgagatcgtc   300
ggcgtcgtca ccgacgtcgg ctccggcgtc acaagcttca agcccggcga cacggtgggc   360
gtgggctact cgtccactc ctgccgcagc tgcgacagct gcagcaaggg gtacgagact   420
actgcccgca ctccgtggag acttccaacg cgttaacctg gacgacgatg acggnggccc   480
acaacaaagg cggttctccg accctctcgt caacaaccta ctttgtccgn cccggcaacc   540
tccgcccccg gggcccnccc tgtntcccgg ntaactt                            577
```

<210> SEQ ID NO 38
<211> LENGTH: 114
<212> TYPE: PRT
<213> ORGANISM: Triticum aestivum

<400> SEQUENCE: 38

```
Met Ala Gly Gly Lys Glu Ala His Gly Trp Ala Ala Arg Asp Val Ser
  1               5                  10                  15

Gly His Leu Ser Pro Tyr His Phe Ser Arg Arg Val Gln Arg Asp Asp
                 20                  25                  30

Asp Val Thr Ile Lys Val Leu Phe Cys Gly Leu Cys His Thr Asp Leu
             35                  40                  45

His Val Ile Lys Asn Glu Phe Gly Asn Ala Lys Tyr Pro Val Val Pro
         50                  55                  60

Gly His Glu Ile Val Gly Val Val Thr Asp Val Gly Ser Gly Val Thr
```

```
                65                  70                  75                  80
Ser Phe Lys Pro Gly Asp Thr Val Gly Val Gly Tyr Phe Val His Ser
                    85                  90                  95

Cys Arg Ser Cys Asp Ser Cys Ser Lys Gly Tyr Glu Thr Thr Ala Arg
                100                 105                 110

Thr Pro

<210> SEQ ID NO 39
<211> LENGTH: 580
<212> TYPE: DNA
<213> ORGANISM: Oryza sativa
<220> FEATURE:
<221> NAME/KEY: unsure
<222> LOCATION: (520)..(521)
<220> FEATURE:
<221> NAME/KEY: unsure
<222> LOCATION: (523)
<220> FEATURE:
<221> NAME/KEY: unsure
<222> LOCATION: (533)
<220> FEATURE:
<221> NAME/KEY: unsure
<222> LOCATION: (577)

<400> SEQUENCE: 39
cttacatgta agctcgtgcc gaattcggca cgagcttaca ctctcatcct ctcctctccc     60
actccacacc caggcaccca gctcgagcgc gactcggcaa atccatggct cccacggcgg    120
cgtcggcggc ggcgggggag gagcagcagg cggtggggct ggcggcgcgc gactcctccg    180
gccacctctc cccttcgcc atctcccgga ggagcactgg agatgacgat gtggcgataa     240
agattctgtt ctgtggaatc tgccactctg acctgcactg catcaagaat gagtggaagc    300
actccatcta cccacttgtt cctgggcacg agatcgccgg tgtggtgacg aagtgggga    360 agaacgtcac caggtttaag gccggtgaca gggtcggcgt ggggtgcatg gtgaactcgt    420
gccggtcatc cgagagctgt aacaatggct tcgagaacca ctgcccggga gggcgtcttc    480
aacctacaac tccgtcgaca aggacgggaa cgtcacctan ngngggttac tcnagcatgg    540
tggtggtgca cgagcgcttc tgggcaagtt cccgggnggg                          580

<210> SEQ ID NO 40
<211> LENGTH: 152
<212> TYPE: PRT
<213> ORGANISM: Oryza sativa
<220> FEATURE:
<221> NAME/KEY: UNSURE
<222> LOCATION: (139)..(140)

<400> SEQUENCE: 40

Met Ala Pro Thr Ala Ala Ser Ala Ala Ala Gly Glu Glu Gln Gln Ala
 1               5                  10                  15

Val Gly Leu Ala Ala Arg Asp Ser Ser Gly His Leu Ser Pro Phe Ala
                20                  25                  30

Ile Ser Arg Arg Ser Thr Gly Asp Asp Val Ala Ile Lys Ile Leu
            35                  40                  45

Phe Cys Gly Ile Cys His Ser Asp Leu His Cys Ile Lys Asn Glu Trp
    50                  55                  60

Lys His Ser Ile Tyr Pro Leu Val Pro Gly His Glu Ile Ala Gly Val
65                  70                  75                  80

Val Thr Glu Val Gly Lys Asn Val Thr Arg Phe Lys Ala Gly Asp Arg
                85                  90                  95
```

```
Val Gly Val Gly Cys Met Val Asn Ser Cys Arg Ser Ser Glu Ser Cys
            100                 105                 110

Asn Asn Gly Phe Glu Asn His Cys Pro Gly Gly Arg Leu Gln Pro Thr
            115                 120                 125

Thr Pro Ser Thr Arg Thr Gly Thr Ser Pro Xaa Xaa Gly Tyr Ser Ser
        130                 135                 140

Met Val Val His Glu Arg Phe
145                 150
```

<210> SEQ ID NO 41
<211> LENGTH: 576
<212> TYPE: DNA
<213> ORGANISM: Glycine max
<220> FEATURE:
<221> NAME/KEY: unsure
<222> LOCATION: (36)
<220> FEATURE:
<221> NAME/KEY: unsure
<222> LOCATION: (56)
<220> FEATURE:
<221> NAME/KEY: unsure
<222> LOCATION: (296)
<220> FEATURE:
<221> NAME/KEY: unsure
<222> LOCATION: (392)
<220> FEATURE:
<221> NAME/KEY: unsure
<222> LOCATION: (410)
<220> FEATURE:
<221> NAME/KEY: unsure
<222> LOCATION: (426)
<220> FEATURE:
<221> NAME/KEY: unsure
<222> LOCATION: (438)
<220> FEATURE:
<221> NAME/KEY: unsure
<222> LOCATION: (471)
<220> FEATURE:
<221> NAME/KEY: unsure
<222> LOCATION: (477)..(478)
<220> FEATURE:
<221> NAME/KEY: unsure
<222> LOCATION: (487)
<220> FEATURE:
<221> NAME/KEY: unsure
<222> LOCATION: (489)
<220> FEATURE:
<221> NAME/KEY: unsure
<222> LOCATION: (504)
<220> FEATURE:
<221> NAME/KEY: unsure
<222> LOCATION: (506)
<220> FEATURE:
<221> NAME/KEY: unsure
<222> LOCATION: (527)
<220> FEATURE:
<221> NAME/KEY: unsure
<222> LOCATION: (534)
<220> FEATURE:
<221> NAME/KEY: unsure
<222> LOCATION: (543)..(544)
<220> FEATURE:
<221> NAME/KEY: unsure
<222> LOCATION: (549)
<220> FEATURE:
<221> NAME/KEY: unsure
<222> LOCATION: (554)

<400> SEQUENCE: 41
cagagatgga gcatccaaag aaggtttttg gttggnctgc tcgggactca tctggncttc     60
tctccccatt caacttctcc agaagagaaa cggggagaa agatttggta ttcaaagtgc    120
aatactgtgg aatatgccac tcagatctac atatgttaaa gaacgagtgg ggcaacacaa    180

-continued

```
cctatcctct ggttcctggg cacgagattg ctggtgtggt aacagaagtt ggaagcaagg      240
tgcaaaagtt caaagttgga gaccgggtag gtgtggggtg catgattgga tcctgngttc      300
atgtgaaagc tgtgatgaaa tcttgagaat tactgcccca aaatgttctc acatacggtg      360
tcaagtattt tgtggaccat aacacatgga gntactctga cttgtggttn ggtgacactt      420
tgtgtngatt cggtaccnac cacttatgct gtctctctct ctgtctggat nctgtgnnag      480
ccttagncnt gacttacact gctnanttgt gtgtgcttgt gacttgnact gcgnagttcc      540
aannttgant atgncatata ccttctacaa agagga                                576
```

```
<210> SEQ ID NO 42
<211> LENGTH: 97
<212> TYPE: PRT
<213> ORGANISM: Glycine max
<220> FEATURE:
<221> NAME/KEY: UNSURE
<222> LOCATION: (12)

<400> SEQUENCE: 42
```

Glu Met Glu His Pro Lys Lys Val Phe Gly Trp Xaa Ala Arg Asp Ser
 1               5                  10                  15

Ser Gly Leu Leu Ser Pro Phe Asn Phe Ser Arg Arg Glu Thr Gly Glu
             20                  25                  30

Lys Asp Leu Val Phe Lys Val Gln Tyr Cys Gly Ile Cys His Ser Asp
         35                  40                  45

Leu His Met Leu Lys Asn Glu Trp Gly Asn Thr Thr Tyr Pro Leu Val
     50                  55                  60

Pro Gly His Glu Ile Ala Gly Val Val Thr Glu Val Gly Ser Lys Val
 65                  70                  75                  80

Gln Lys Phe Lys Val Gly Asp Arg Val Gly Val Gly Cys Met Ile Gly
                 85                  90                  95

Ser

```
<210> SEQ ID NO 43
<211> LENGTH: 502
<212> TYPE: DNA
<213> ORGANISM: Triticum aestivum
<220> FEATURE:
<221> NAME/KEY: unsure
<222> LOCATION: (382)
<220> FEATURE:
<221> NAME/KEY: unsure
<222> LOCATION: (400)
<220> FEATURE:
<221> NAME/KEY: unsure
<222> LOCATION: (465)

<400> SEQUENCE: 43
```

```
cgaacgtcta atcgcctcac acacaggaaa ggcaaaaaag aaaccaaaac ctccggggag       60
ttactctaga gatttccggc ggaacctcgc gtcaggatgg cacccacggc gacggcggcg      120
gagcagagcc agcagcacac gaagaaggcg gtgggtctgg cggcgctcga cgcctccggc      180
cacctctccc cgctcgccat cacccgaagg agcaccggag atgacgatgt cgtgataaag      240
attctgtact gcgggatctg ccactctgac ctgcacagca tcaagaacga ctggaagaac      300
gccaagtacc ccatgattcc cgggcacgag atcgccggcg aggtcaccga ggtcggcaag      360
aacgtgacca agttcaaggc angcgaccgt gtcggcgtcn ggtgcatggt gaactcctgc      420
caatcctgcg aaaactgcga caagggcttc gagaatcact gccnggcat gatttcaact      480
```
acaactccgt cgacgtgacg ga            502

<210> SEQ ID NO 44
<211> LENGTH: 128
<212> TYPE: PRT
<213> ORGANISM: Triticum aestivum
<220> FEATURE:
<221> NAME/KEY: UNSURE
<222> LOCATION: (96)
<220> FEATURE:
<221> NAME/KEY: UNSURE
<222> LOCATION: (102)

<400> SEQUENCE: 44

```
Met Ala Pro Thr Ala Thr Ala Glu Gln Ser Gln Gln His Thr Lys
 1               5                  10                  15

Lys Ala Val Gly Leu Ala Ala Leu Asp Ala Ser Gly His Leu Ser Pro
                20                  25                  30

Leu Ala Ile Thr Arg Arg Ser Thr Gly Asp Asp Asp Val Val Ile Lys
            35                  40                  45

Ile Leu Tyr Cys Gly Ile Cys His Ser Asp Leu His Ser Ile Lys Asn
        50                  55                  60

Asp Trp Lys Asn Ala Lys Tyr Pro Met Ile Pro Gly His Glu Ile Ala
65                  70                  75                  80

Gly Glu Val Thr Glu Val Gly Lys Asn Val Thr Lys Phe Lys Ala Xaa
                85                  90                  95

Asp Arg Val Gly Val Xaa Cys Met Val Asn Ser Cys Gln Ser Cys Glu
            100                 105                 110

Asn Cys Asp Lys Gly Phe Glu Asn His Cys Pro Gly Met Ile Ser Thr
        115                 120                 125
```

<210> SEQ ID NO 45
<211> LENGTH: 744
<212> TYPE: DNA
<213> ORGANISM: Glycine max
<220> FEATURE:
<221> NAME/KEY: unsure
<222> LOCATION: (538)
<220> FEATURE:
<221> NAME/KEY: unsure
<222> LOCATION: (574)
<220> FEATURE:
<221> NAME/KEY: unsure
<222> LOCATION: (588)
<220> FEATURE:
<221> NAME/KEY: unsure
<222> LOCATION: (614)
<220> FEATURE:
<221> NAME/KEY: unsure
<222> LOCATION: (652)
<220> FEATURE:
<221> NAME/KEY: unsure
<222> LOCATION: (686)..(687)
<220> FEATURE:
<221> NAME/KEY: unsure
<222> LOCATION: (690)
<220> FEATURE:
<221> NAME/KEY: unsure
<222> LOCATION: (701)
<220> FEATURE:
<221> NAME/KEY: unsure
<222> LOCATION: (707)
<220> FEATURE:
<221> NAME/KEY: unsure
<222> LOCATION: (711)
<220> FEATURE:
<221> NAME/KEY: unsure
<222> LOCATION: (717)
<220> FEATURE:

```
<221> NAME/KEY: unsure
<222> LOCATION: (725)
<220> FEATURE:
<221> NAME/KEY: unsure
<222> LOCATION: (734)
<220> FEATURE:
<221> NAME/KEY: unsure
<222> LOCATION: (741)

<400> SEQUENCE: 45
cacaagtgtg agaaaaatta tgagttccaa aggtgttggt gaggattgcc tgggatgggc    60
agcaagagat gcatccggag ttctatcacc ttacaaattc agtcgcagga ctcttgggaa   120
tgaagatgtt catattaaaa ttacgcactg tggtgtttgc ttcgctgatg tagtttggac   180
aaggaataaa catggtgact caaagtatcc tgtcgtgcct ggtcacgaga ttgctgggat   240
tgtgacaaag gttggctcca atgtccaccg tttaaggtt ggtgaccatg ttggagtggg    300
gacttatgtc aactcatgta gggattgtga acattgtaat gacagagaag aagttcattg   360
taccaaggga tctgttttca cttttaatgg tgttgatttt gatggtacaa ttacaaaagg   420
aggatactcc agttacatag tagtccatga gaggtactgc ttcacgatac caaaaagcta   480
tccattggct tcagcagctc ctttgctttg tgctggaatt acagtttatt caccgatngt   540
gcgccacaaa gatgaatcaa cctggtaaat cccntgggag tgattggncc tggtggcccc   600
ccgtcaaatg gcantgaaat ttggaaaagg catttggttt gagtgtgaca cntttcacca   660
ccatcatatc caacaaagag ggcggnnccn gaaccccctt nggtggncac naaattnttg   720
tttcncccca atcncaaagg naat                                          744

<210> SEQ ID NO 46
<211> LENGTH: 172
<212> TYPE: PRT
<213> ORGANISM: Glycine max

<400> SEQUENCE: 46

Met Ser Ser Lys Gly Val Gly Glu Asp Cys Leu Gly Trp Ala Ala Arg
  1               5                  10                  15

Asp Ala Ser Gly Val Leu Ser Pro Tyr Lys Phe Ser Arg Arg Thr Leu
             20                  25                  30

Gly Asn Glu Asp Val His Ile Lys Ile Thr His Cys Gly Val Cys Phe
         35                  40                  45

Ala Asp Val Val Trp Thr Arg Asn Lys His Gly Asp Ser Lys Tyr Pro
     50                  55                  60

Val Val Pro Gly His Glu Ile Ala Gly Ile Val Thr Lys Val Gly Ser
 65                  70                  75                  80

Asn Val His Arg Phe Lys Val Gly Asp His Val Gly Val Gly Thr Tyr
                 85                  90                  95

Val Asn Ser Cys Arg Asp Cys Glu His Cys Asn Asp Arg Glu Glu Val
            100                 105                 110

His Cys Thr Lys Gly Ser Val Phe Thr Phe Asn Gly Val Asp Phe Asp
        115                 120                 125

Gly Thr Ile Thr Lys Gly Gly Tyr Ser Ser Tyr Ile Val Val His Glu
    130                 135                 140

Arg Tyr Cys Phe Thr Ile Pro Lys Ser Tyr Pro Leu Ala Ser Ala Ala
145                 150                 155                 160

Pro Leu Leu Cys Ala Gly Ile Thr Val Tyr Ser Pro
                165                 170
```

```
<210> SEQ ID NO 47
<211> LENGTH: 656
<212> TYPE: DNA
<213> ORGANISM: Triticum aestivum
<220> FEATURE:
<221> NAME/KEY: unsure
<222> LOCATION: (453)
<220> FEATURE:
<221> NAME/KEY: unsure
<222> LOCATION: (485)..(486)
<220> FEATURE:
<221> NAME/KEY: unsure
<222> LOCATION: (508)
<220> FEATURE:
<221> NAME/KEY: unsure
<222> LOCATION: (525)
<220> FEATURE:
<221> NAME/KEY: unsure
<222> LOCATION: (541)
<220> FEATURE:
<221> NAME/KEY: unsure
<222> LOCATION: (559)
<220> FEATURE:
<221> NAME/KEY: unsure
<222> LOCATION: (574)
<220> FEATURE:
<221> NAME/KEY: unsure
<222> LOCATION: (576)
<220> FEATURE:
<221> NAME/KEY: unsure
<222> LOCATION: (584)..(585)
<220> FEATURE:
<221> NAME/KEY: unsure
<222> LOCATION: (588)
<220> FEATURE:
<221> NAME/KEY: unsure
<222> LOCATION: (634)
<220> FEATURE:
<221> NAME/KEY: unsure
<222> LOCATION: (651)

<400> SEQUENCE: 47
ctcgtgccga attcggcacg aggaacgacc tcggtgcttc gaagtacccc atggtcccag      60
ggcatgaggt ggttggcgag gtggtggagg tcgggccgga ggtgagcaag ttccgggccg     120
gcgacgtggt gggcgtgggg gtgatcgtgg ggtgctgccg cgactgccgg ccgtgcaagg     180
ccaacgtcga gcagtactgc aacaagaaga tctggtcgta caacgacgtc tacaccgacg     240
gcaagccgac gcagggcggc ttcgcctccg ccatggtcgt cgatcagaag ttcgtggtga     300
agatccccgc cgggctggcg ccggagcagg cggcgccgct gctgtgcgcg ggggtgacgg     360
tgtacagccc gctgaagcac ttcgggctca tgaccccggg cctccgcggc gggatactgg     420
gcctgggcgg cgttgggcca catggcgtgn aangtggcaa atccatggcc acaacgtgac     480
gtgannactc gtccaacaag aacggccnag gcatggacac tgggngccga gcgtactcgt     540
nactccgaca ccgacaaang gccccgccgc cganccctgg atanncanca cacgtgccgc     600
caacaccgct ggacctactg cctctaagtg acgnaactgt ctatgctgat ncgacc        656

<210> SEQ ID NO 48
<211> LENGTH: 155
<212> TYPE: PRT
<213> ORGANISM: Triticum aestivum
<220> FEATURE:
<221> NAME/KEY: UNSURE
<222> LOCATION: (151)

<400> SEQUENCE: 48

Arg Ala Glu Phe Gly Thr Arg Asn Asp Leu Gly Ala Ser Lys Tyr Pro
 1               5                  10                  15
```

-continued

```
Met Val Pro Gly His Glu Val Val Gly Glu Val Val Glu Val Gly Pro
             20                  25                  30

Glu Val Ser Lys Phe Arg Ala Gly Asp Val Val Gly Val Gly Val Ile
         35                  40                  45

Val Gly Cys Cys Arg Asp Cys Arg Pro Cys Lys Ala Asn Val Glu Gln
     50                  55                  60

Tyr Cys Asn Lys Lys Ile Trp Ser Tyr Asn Asp Val Tyr Thr Asp Gly
 65                  70                  75                  80

Lys Pro Thr Gln Gly Gly Phe Ala Ser Ala Met Val Val Asp Gln Lys
             85                  90                  95

Phe Val Val Lys Ile Pro Ala Gly Leu Ala Pro Glu Gln Ala Ala Pro
            100                 105                 110

Leu Leu Cys Ala Gly Val Thr Val Tyr Ser Pro Leu Lys His Phe Gly
        115                 120                 125

Leu Met Thr Pro Gly Leu Arg Gly Gly Ile Leu Gly Leu Gly Gly Val
        130                 135                 140

Gly Pro His Gly Arg Glu Xaa Gly Lys Ser Met
145                 150                 155
```

PLANT CINNAMYL-ALCOHOL DEHYDROGENASE HOMOLOGS

This application is a divisional of application Ser. No. 09/501,115 filed Feb. 9, 2000, now U.S. Pat. No. 6,552,249, which claims benefit of Provisional Application No. 60/119,585 filed Feb. 10,1999, now expired.

FIELD OF THE INVENTION

This invention is in the field of plant molecular biology. More specifically, this invention pertains to nucleic acid fragments encoding lignin biosynthetic enzymes in plants and seeds.

BACKGROUND OF THE INVENTION

Plant cells and tissues can respond to mechanical, chemical or pathogen induced injury by producing various phenolic compounds including mono- or dimethoxylated lignin precursors derived from cinnamic acid via a complex series of biochemical reactions. These lignin precursors are eventually used by the plant to produce the phenolic macromolecule lignin which helps in wound repair by adding hydrophobicity, a physical barrier against pathogen infection and mechanical strength to the injured tissue (Vance, C. P., et al., 1980, *Annu Rev Phytopathol* 18:259–288).

Cinnamyl-alcohol dehydrogenase (CAD) catalyzes the final step in the production of lignin monomers and has been implicated in plant defense response to fungal infection. Because of lignins importance in cell wall architecture and wound repair mechanisms there is considerable interest in the prospects for altering lignin quantity or quality by genetic engineering. For example, chemical treatments needed to remove lignin during the paper-pulping process are expensive and environmentally unfriendly. Plants with altered lignin quantity or quality could benefit this industry (Boudet, A., et al., 1996, *Mol Breeding* 2:25–39; Campbell, M., et al., 1996, *Plant Physiol* 110:3–13). Also, during soybean seed storage and processing lignin monomers are often oxidized, via polyphenol oxidase, to compounds that impart an undesirable yellow color to soybean seeds and seed products. It may be possible to reduce the amount of these phenolic compounds by suppressing CAD activity.

Cinnamyl-alcohol dehydrogenase genes described herein appear to be part of a multigene family. This application details the discovery of several different CAD genes from rice, soybean and wheat. Based on homology each of the genes (which range from 24% to 82% in similarity) have been placed into one of five different sub-groups that make up the CAD multigene family. There is a great deal of interest in identifying the genes that encode proteins involved in the production of lignin in plants. These genes may be used in plant cells to control lignin production. Accordingly, the availability of nucleic acid sequences encoding all or a portion of an enzyme involved in the production of lignin would facilitate studies to better understand lignin production in plants and provide genetic tools to enhance or otherwise alter lignin biosynthesis which in turn could provide mechanisms to control cell wall architecture, host defense and injury repair mechanisms and reduce the pool of phenolic compounds in plant cells.

SUMMARY OF THE INVENTION

The present invention relates to isolated polynucleotides comprising a nucleotide sequence encoding a polypeptide of at least 200 amino acids that has at least 92% identity based on the Clustal method of alignment when compared to a polypeptide selected from the group consisting of a corn cinnamyl-alcohol dehydrogenase polypeptide of SEQ ID NO:8, rice cinnamyl-alcohol dehydrogenase polypeptides of SEQ ID NOs:2 and 10, soybean cinnamyl-alcohol dehydrogenase polypeptides of SEQ ID NOs:4, 12, 20, 28, 30 and 34, and wheat cinnamyl-alcohol dehydrogenase polypeptides of SEQ ID NOs:6, 14 and 32. The present invention also relates to an isolated polynucleotide comprising the complement of the nucleotide sequences described above.

The present invention also relates to isolated polynucleotides comprising a nucleotide sequence encoding a polypeptide of at least 103 amino acids that has at least 80% identity based on the Clustal method of alignment when compared to a polypeptide selected from the group consisting of a corn cinnamyl-alcohol dehydrogenase polypeptide of SEQ ID NO:26, a rice cinnamyl-alcohol dehydrogenase polypeptide of SEQ ID NO:18 and wheat cinnamyl-alcohol dehydrogenase polypeptides of SEQ ID NOs:22 and 24. The present invention also relates to an isolated polynucleotide comprising the complement of the nucleotide sequences described above.

The present invention also relates to isolated polynucleotides comprising a nucleotide sequence encoding a polypeptide of at least 186 amino acids that has at least 80% identity based on the Clustal method of alignment when compared to a corn cinnamyl-alcohol dehydrogenase polypeptide of SEQ ID NO:16. The present invention also relates to an isolated polynucleotide comprising the complement of the nucleotide sequences described above.

It is preferred that the isolated polynucleotides of the claimed invention consists of a nucleic acid sequence selected from the group consisting of SEQ ID NOs:1, 3, 5, 7, 9, 11, 13, 15, 17, 19, 21, 23, 25, 27, 29, 31, 33, 35, 37, 39, 41, 43, 45 and 47 that codes for the polypeptide selected from the group consisting of SEQ ID NOs:2, 4, 6, 8, 10, 12, 14, 16, 18, 20, 22, 24, 26, 28, 30, 32, 34, 36, 38, 40, 42, 44, 46 and 48. The present invention also relates to an isolated polynucleotide comprising a nucleotide sequences of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a cinnamyl-alcohol dehydrogenase polypeptide of at least 200 amino acids comprising at least 92% homology based on the Clustal method of alignment compared to a polypeptide selected from the group consisting of SEQ ID NOs:2, 4, 6, 8, 10, 12, 14, 20, 28, 30, 32 and 34.

The present invention relates to a cinnamyl-alcohol dehydrogenase polypeptide of at least 103 amino acids comprising at least 80% homology based on the Clustal method of alignment compared to a polypeptide selected from the group consisting of SEQ ID NOs:18, 22, 24 and 26.

The present invention relates to a cinnamyl-alcohol dehydrogenase polypeptide of at least 186 amino acids comprising at least 80% homology based on the Clustal method of alignment compared to a polypeptide of SEQ ID NO:16.

The present invention relates to a method of selecting an isolated polynucleotide that affects the level of expression of a cinnamyl-alcohol dehydrogenase polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level a cinnamyl-alcohol dehydrogenase polypeptide in the host cell containing the isolated polynucleotide; and (d) comparing the level of a cinnamyl-alcohol dehydrogenase polypeptide in the host cell containing the isolated polynucleotide with the level of a cinnamyl-alcohol dehydrogenase polypeptide in the host cell that does not contain the isolated polynucleotide.

The present invention relates to a method of obtaining a nucleic acid fragment encoding a substantial portion of a cinnamyl-alcohol dehydrogenase polypeptide gene, preferably a plant cinnamyl-alcohol dehydrogenase polypeptide gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47, and the complement of such nucleotide sequences; and amplifying a nucleic acid fragment (preferably a cDNA inserted in a cloning vector) using the oligonucleotide primer. The amplified nucleic acid fragment preferably will encode a portion of a cinnamyl-alcohol dehydrogenase amino acid sequence.

The present invention also relates to a method of obtaining a nucleic acid fragment encoding all or a substantial portion of the amino acid sequence encoding a cinnamyl-alcohol dehydrogenase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

The present invention relates to a composition, such as a hybridization mixture, comprising an isolated polynucleotide of the present invention.

The present invention relates to an isolated polynucleotide of the present invention comprising at least one of 30 contiguous nucleotides derived from a nucleic acid sequence selected from the group consisting of SEQ ID NOs:1, 3, 5, 7, 9, 11, 13, 15, 17, 19, 21, 23, 25, 27, 29, 31, 33, 35, 37, 39, 41, 43, 45 and 47.

The present invention relates to an expression cassette comprising an isolated polynucleotide of the present invention operably linked to a promoter.

The present invention relates to a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the cinnamyl-alcohol dehydrogenase polynucleotide in an amount sufficient to complement a null mutant with altered cinnamyl-alcohol dehydrogenase activity and lignin production to provide a positive selection means.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"). Nucleotide sequences, SEQ ID NOs:1, 5, 9, 11, 13, 19 and 33 and amino acid sequences SEQ ID NOs:2, 6, 10, 12, 14, 20 and 34 were determined by further sequence analysis of cDNA clones encoding the amino acid sequences set forth in SEQ ID NOs:36, 38, 40, 42, 44, 46 and 48. Nucleotide SEQ ID NOs:35, 37, 39, 41. 43, 45 and 47 and amino acid SEQ ID NOs: 36, 38, 40, 42, 44, 46 and 48 were presented in a U.S. Provisional Application No. 60/119,585, filed Feb. 10, 1999.

The sequence descriptions and Sequence Listing attached hereto comply with the rules governing nucleotide and/or amino acid sequence disclosures in patent applications as set forth in 37 C.F.R. §1.821–1.825.

TABLE 1

Lignin Biosynthetic Enzymes

| Protein | Clone Designation | SEQ ID NO: (Nucleotide) | (Amino Acid) |
|---|---|---|---|
| Cinnamyl-alcohol Dehydrogenase Type 1 | rls6.pk0033.h11 CGS | 1 | 2 |
| Cinnamyl-alcohol Dehydrogenase Type 1 | se4.pk0015.f6 CGS | 3 | 4 |
| Cinnamyl-alcohol Dehydrogenase Type 1 | wl1n.pk0095.d1 CGS | 5 | 6 |
| Cinnamyl-alcohol Dehydrogenase Type 2 | Contig composed of: csi1.pk0027.a12 csi1n.pk0007.g8 cta1n.pk0006.a5 cta1n.pk0073.g7 p0076.cwhag79r p0089.csdcj42r | 7 | 8 |
| Cinnamyl-alcohol Dehydrogenase Type 2 | rl0n.pk098.a8 CGS | 9 | 10 |
| Cinnamyl-alcohol Dehydrogenase Type 2 | ssm.pk0030.d9 CGS | 11 | 12 |
| Cinnamyl-alcohol Dehydrogenase Type 2 | wdk2c.pk005.k24 CGS | 13 | 14 |
| Cinnamyl-alcohol Dehydrogenase Type 3 | Contig composed of: cpflc.pk007.j10 p0089.csdca31rb | 15 | 16 |

TABLE 1-continued

Lignin Biosynthetic Enzymes

| Protein | Clone Designation | SEQ ID NO: (Nucleotide) | SEQ ID NO: (Amino Acid) |
|---|---|---|---|
| Cinnamyl-alcohol Dehydrogenase Type 3 | rdr1f.pk005.n7 EST | 17 | 18 |
| Cinnamyl-alcohol Dehydrogenase Type 3 | sfl1.pk0063.e7 CGS | 19 | 20 |
| Cinnamyl-alcohol Dehydrogenase Type 3 | wle1n.pk0062.c3 EST | 21 | 22 |
| Cinnamyl-alcohol Dehydrogenase Type 3 | Contig composed of: w1m96.pk056.k10 wre1n.pk0020.f6 | 23 | 24 |
| Cinnamyl-alcohol Dehydrogenase Type 4 | p0041.crtbq05r EST | 25 | 26 |
| Cinnamyl-alcohol Dehydrogenase Type 4 | Contig composed of: sfl1d.pk125.h20 src2c.pk008.p22 sre.pk0026.c10 sre.pk0059.a1 | 27 | 28 |
| Cinnamyl-alcohol Dehydrogenase Type 5 | Contig composed of: se3.03g03 ses9c.pk003.j22 sfl1.pk128.g18 sgs1c.pk003.e18 sgs4c.pk006.a4 | 29 | 30 |
| Cinnamyl-alcohol Dehydrogenase Type 5 | Contig composed of: w1m96.pk0014.c9 w1m96.pk029.p17 wre1n.pk0039.f5 | 31 | 32 |
| Cinnamyl-alcohol Dehydrogenase Type 5 | sls1c.pk001.p19 CGS | 33 | 34 |
| Cinnamyl-alcohol Dehydrogenase Type 1 | Contig composed of: rls6.pk0033.h11 rls6.pk0069.f10 | 35 | 36 |
| Cinnamyl-alcohol Dehydrogenase Type 1 | Contig composed of: wl1n.pk0095.d1 wl1n.pk151.f3 | 37 | 38 |
| Cinnamyl-alcohol Dehydrogenase Type 2 | Contig composed of: rl0n.pk096.j8 rl0n.pk098.a8 | 39 | 40 |
| Cinnamyl-alcohol Dehydrogenase Type 2 | ssm.pk0030.d9 EST | 41 | 42 |
| Cinnamyl-alcohol Dehydrogenase Type 2 | Contig composed of: wdk1c.pk006.j22 wdk2c.pk005.k24 | 43 | 44 |
| Cinnamyl-alcohol Dehydrogenase Type 3 | Contig composed of: sdp2c.pk002.d1 sfl1.pk0063.e7 srr1c.pk002.j18 | 45 | 46 |
| Cinnamyl-alcohol Dehydrogenase Type 5 | Contig composed of: wlm96.pk029.p17 wlmk4.pk0004.g5 | 47 | 48 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs: 1, 3, 5, 7, 9, 11, 13, 15, 17, 19, 21, 23, 25, 27, 29, 31, 33, 35, 37, 39, 41, 43, 45, 47 or the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47 and the complement of such nucleotide sequences may be used in methods of selecting an isolated polynucleotide that affects the expression of a polypeptide (cinnamyl-alcohol dehydrogenase) in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several lignin biosynthetic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other cinnamyl-alcohol dehydrogenase proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohnian and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45 and 47, the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as cinnamyl-alcohol dehydrogenase) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide (cinnamyl-alcohol dehydrogenase).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of cinnamyl-alcohol dehydrogenase activity in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded lignin biosynthetic enzyme. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes.

Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cpf1c | Corn pooled BMS treated with chemicals related to protein synthesis** | cpf1c.pk007.j10 |
| csi1n | Corn Silk* | csi1.pk0027.a12 csi1n.pk0007.g8 |

TABLE 2-continued cDNA Libraries from Corn, Rice, Soybean and Wheat

| Library | Tissue | Clone |
|---|---|---|
| cta1n | Corn Tassel* | cta1n.pk0006.a5 |
|  |  | cta1n.pk0073.g7 |
| p0015 | Corn Embryo 13 Days After Pollination | p0015.cdpeb84rb |
| p0037 | Corn V5 Stage Roots Infested With Corn Root Worm*** | p0037.crwae78rb |
| p0041 | Corn Tassel: Apical Meristem > Floral Transition | p0041.crtbq05r |
| p0076 | Corn (V6–V7) whorl/leaf tissue following European corn borer infestation | p0076.cwhag79r |
| p0089 | Corn 10 day Seedling, germination with cold stress, (growth at cycle of 16C for 8 hours, light and 14C for 16 hours in dark) | p0089.csdcj42r |
|  |  | p0089.csdea31rb |
| rdr1f | Rice Developing Root of 10 Day Old Plant | rdr1f.pk005.n7 |
| rds2c | Rice Developing Seeds From Middle of the Plant | rds2c.pk007.j10 |
| rl0n | Rice 15 Day Old Leaf* | rl0n.pk098.a8 |
|  |  | rl0n.pk096.j8 |
| rls6 | Rice Leaf 15 Days After Germination, 6 Hours After Infection of Strain *Magaporthe grisea* 4360-R-67 (AVR2-YAMO); Susceptible | rls6.pk0033.h11 |
|  |  | rls6.pk0069.f10 |
| rsr9n | Rice Leaf 15 Days After Germination Harvested 2–72 Hours Following Infection With *Magnaporia grisca* (4360-R-62 and 4360-R-67)* | rsr9n.pk001.i24 |
| sdp2c | Soybean Developing Pods (6–7 mm) | sdp2c.pk002.d1 |
| se3 | Soybean Embryo, 17 Days After Flowering | se3.03g03 |
| se4 | Soybean Embryo, 19 Days After Flowering | se4.pk0015.f6 |
| ses9c | Soybean Embryogenic Suspension | ses9c.pk003.j22 |
| sfl1 | Soybean Immature Flower | sfl1.pk0063.e7 |
|  |  | sf1.pk125.h20 |
|  |  | sf1.pk128.g18 |
| sgs1c | Soybean Seeds 4 Hours After Germination | sgs1c.pk003.e18 |
| sgs4c | Soybean Seeds 2 Days After Germination | sgs4c.pk006.a4 |
| sls1c | Soybean Infected With *Sclerotinia sclerotiorum* Mycelium | sls1c.pk001.p19 |
| src2c | Soybean 8 Day Old Root Infected With Cyst Nematode *Heterodera glycinis* | src2c.pk008.p22 |
| sre | Soybean Root Elongation Zone 4 to 5 Days After Germination | sre.pk0026.c10 |
|  |  | sre.pk0059.a1 |
| srr1c | Soybean 8-Day-Old Root | srr1c.pk002.j18 |
| ssm | Soybean Shoot Meristem | ssm.pk0030.d9 |
|  |  | wdk1c.pk006.j22 |
| wdk2c | Wheat Developing Kernel, 7 Days After Anthesis | wdk2c.pk005.k24 |
| wl1n | Wheat Leaf From 7 Day Old Seedling* | wl1n.pk0095.d1 |
| wle1n | Wheat Leaf From 7 Day Old Etiolated Seedling* | wle1n.pk0062.c3 |
|  |  | wl1n.pk151.f3 |
| wlm96 | Wheat Seedlings 96 Hours After Inoculation With *Erysiphe graminis* f. sp tritici | wlm96.pk0014.c9 |
|  |  | wlm96.pk029.p17 |
|  |  | wlm96.pk056.k10 |
| wlmk4 | Wheat Seedlings 4 Hours After Inoculation With *Erysiphe graminis* f sp tritici and treatment with Herbicide**** | wlmk4.pk0004.g5 |
| wre1n | Wheat Root From 7 Day Old Etiolated Seedling* | wre1n.pk0020.f6 |
|  |  | wre1n.k0039.f5 |

*These libraries were normalized essentially as described in U.S. Pat. No. 5,482,845, incorporated herein by reference.
**Chemicals used included chloramphenicol, cyclohexamide, aurintricarboylic acid
***Corn developmental stages are explained in the publication "How a corn plant develops" from the Iowa State University Coop. Ext. Service Special Report No. 48 reprinted June 1993.
****Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding lignin biosynthetic enzymes were identified by conducting BLAST (Basic Local Alignment Search Tool; Altschul et al. (1993) *J. Mol. Biol.* 215:403–410; searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) Nat. Genet. 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Cinnamyl-Alcohol Dehydrogenase

The BLASTX search using the EST sequences from clones listed in Table 3 revealed similarity of the polypeptides encoded by the cDNAs to cinnamyl-alcohol dehydrogenase from *Fragaria x ananassa* (NCBI Identifier No. gi 4097522), *Medicago sativa* (NCBI Identifier No. 3603401), *Mesembryanthemum crystallinum* (NCBI Identifier No. gi 1724110), *Arabidopsis thaliana* (NCBI Identifier No. 6648160), *Stylosanthes humilis* (NCBI Identifier No. gi 3913194), *Aralia cordata* (NCBI Identifier No. 1168727), *Medicago sative* (NCBI Identifier No. gi 399168), *Lolium perene* (NCBI Identifier No. gi 3913181 and *Saccharomyces cerevisiae* (NCBI Identifier No. gi 6323980). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to *Fragaria x ananassa, Medicago sativa, Mesembryanthemum crystallinum, Arabidopsis thaliana, Stylosanthes humilis, Aralia cordata, Lolium perene* and *Saccharomyces cerevisiae* Cinnamyl-Alcohol Dehydrogenase

| Clone | Status | BLAST pLog Score |
| --- | --- | --- |
| rls6.pk0033.h11 | CGS | 127.00 (gi 4097522) |
| se4.pk0015.f6 | CGS | >254.00 (gi 3603401) |
| wl1n.pk0095.d1 | CGS | 124.00 (gi 1724110) |
| Contig composed of: csi1.pk0027.a12 csi1n.pk0007.g8 ctaln.pk0006.a5 ctaln.pk0073.g7 p0076.cwhag79r p0089.csdcj42r | CGS | 135.00 (gi 1724110) |
| rl0n.pk098.a8 | CGS | 133.00 (gi 1724110) |
| ssm.pk0030.d9 | CGS | 175.00 (gi 4097522) |
| wdk2c.pk005.k24 | CGS | 138.00 (gi 1724110) |

TABLE 3-continued

BLAST Results for Sequences Encoding Polypeptides Homologous to *Fragaria x ananassa, Medicago sativa, Mesembryanthemum crystallinum, Arabidopsis thaliana, Stylosanthes humilis, Aralia cordata, Lolium perene* and *Saccharomyces cerevisiae* Cinnamyl-Alcohol Dehydrogenase

| Clone | Status | BLAST pLog Score |
| --- | --- | --- |
| Contig composed of: cpflc.pk007.j10 p0089.csdca31rb | Contig | 78.30 (gi 6648160) |
| rdr1f.pk005.n7 | EST | 41.22 (gi 6648160) |
| sfl1.pk0063.e7 | CGS | 101.00 (gi 1724110) |
| wle1n.pk0062.c3 | EST | 40.15 (gi 3913194) |
| Contig composed of: wlm96.pk056.k10 wre1n.pk0020.f6 | Contig | 79.70 (gi 6648160) |
| p0041.crtbq05r | EST | 22.52 (gi 1168727) |
| Contig composed of: sfl1.pk125.h20 src2c.pk008.p22 sre.pk0026.c10 sre.k0059.a1 | Contig | 108.00 (gi 1724110) |
| Contig composed of: se3.03g03 ses9c.pk003.j22 sfl1.pk128.g18 sgs1c.pk003.e18 sgs4c.pk006.a4 | CGS | >254.00 (gi 399168) |
| Contig composed of: wlm96.pk0014.c9 wlm96.pk029.p17 wre1n.pk0039.f5 | CGS | >254.00 (gi 3913181) |
| sls1c.pk001.p19 | CGS | 101.00 (gi 6323980) |

The data in Table 4 represents a calculation of the percent identity of the amino acid sequences set forth in SEQ ID NOs:2, 4, 6, 8, 10, 12, 14, 16, 18, 20, 22, 24, 26, 28, 30, 32 and 34 and the *Fragaria x ananassa, Medicago sativa, Mesembryanthemum crystallinum, Arabidopsis thaliana, Stylosanthes humilis, Aralia cordata, Lolium perene* and *Saccharomyces cerevisiae* sequences. The percent identity between SEQ ID NOs:2, 4, 6, 8, 10, 12, 14, 16, 18, 20, 22, 24, 26, 28, 30, 32 and 34 ranged from 24% to 82%.

TABLE 4

Percent Identity of Amino Acid Sequences Deduced From the Nucleotide Sequences of cDNA Clones Encoding Polypeptides Homologous to *Fragaria x ananassa, Medicago sativa, Mesembryanthemum crystallnum, Arabidopsis thaliana, Stylosanthes humilis, Aralia cordata, Lolium perene* and *Saccharomyces cerevisiae* Cinnamyl-Alcohol Dehydrogenase

| SEQ ID NO. | Percent Identity to |
| --- | --- |
| 2 | 60% (gi 4097522) |
| 4 | 84% (gi 3603401) |
| 6 | 58% (gi 1724110) |
| 8 | 64% (gi 1724110) |
| 10 | 62% (gi 1724110) |
| 12 | 81% (gi 4097522) |
| 14 | 64% (gi 1724110) |
| 16 | 64% (gi 6648160) |
| 18 | 65% (gi 6648160) |
| 20 | 49% (gi 1724110) |
| 22 | 56% (gi 3913194) |
| 24 | 77% (gi 6648160) |
| 26 | 54% (gi 1168727) |
| 28 | 54% (gi 1724110) |
| 30 | 87% (gi 399168) |
| 32 | 91% (gi 3913181) |
| 34 | 49% (gi 6323980) |

Sequence alignments and percent identity calculations were performed using the Megalign program of the LASER- GENE bioinformatics computing suite (DNASTAR Inc., Madison, Wis.) Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a cinnamyl-alcohol dehydrogenase. These sequences represent the corn, rice, soybean and wheat sequences encoding cinnamyl-alcohol dehydrogenase.

Example 4
Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5
Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin.

Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methyl-sulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising:
   (a) a nucleotide sequence encoding a polypeptide having cinnamyl-alcohol dehydrogenase activity, wherein the amino acid sequence of the polypeptide and the amino acid sequence of SEQ ID NO: 10 have at least 92% sequence identity based on the Clustal alignment method, or
   (b) the complement of the nucleotide sequence, wherein the complement contains the same number of nucleotides as the nucleotide sequence, and the complement and the nucleotide sequence are 100% complementary.

2. The polynucleotide of claim 1, wherein the amino acid sequence of the polypeptide and the amino acid sequence of SEQ ID NO:10 have at least 95% sequence identity based on the Clustal alignment method.

3. The polynucleotide of claim 1, wherein the nucleotide sequence comprises the nucleotide sequence of SEQ ID NO:9.

4. The polynucleotide of claim 1, wherein the polypeptide comprises the amino acid sequence of SEQ ID NO:10.

5. A vector comprising the polynucleotide of claim 1.

6. A recombinant DNA construct comprising the polynucleotide of claim 1 operably linked to a regulatory sequence.

7. A method for transforming a cell comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

* * * * *